United States Patent [19]
Onuki et al.

[11] Patent Number: 5,662,666
[45] Date of Patent: Sep. 2, 1997

[54] LIGATIVE SUTURER

[75] Inventors: Takamasa Onuki, 150 Yamashita-cho, Naka-ku, Yokohama-cho, Kanagawa; Masayoshi Yokoyama, Tokyo; Tetsuya Yamamoto, Osaka, all of Japan

[73] Assignees: Takamasa Onuki, Kanagawa; Masayoshi Yokoyama, Tokyo; Sugan Co., Ltd., Osaka, all of Japan

[21] Appl. No.: 623,265

[22] Filed: Mar. 28, 1996

[30] Foreign Application Priority Data

Nov. 13, 1995 [JP] Japan ................. 7-294208

[51] Int. Cl.⁶ ........................................... A61B 17/00
[52] U.S. Cl. ........................ 606/148; 606/139; 606/144; 289/17; 112/169
[58] Field of Search ........................... 606/139, 144, 606/148, 151, 143; 112/169; 289/17

[56] References Cited

U.S. PATENT DOCUMENTS

| | | | |
|---|---|---|---|
| 5,423,833 | 6/1995 | Zauza | 606/148 |
| 5,484,095 | 1/1996 | Green et al. | 606/143 |
| 5,562,682 | 10/1996 | Oberlin et al. | 606/143 |

FOREIGN PATENT DOCUMENTS 7-51274  2/1995  Japan.

*Primary Examiner*—Jeffrey A. Schmidt
*Attorney, Agent, or Firm*—Lowe, Price, LeBlanc & Becker

[57] ABSTRACT

A ligative suturer according to the present invention comprises a first rod which is connected with a ligative sutural member, and a second rod which is connected with the first rod to be bendable in the horizontal direction (L, R). A thread guard member which is capable of protrusion and storage is provided in the first rod, while a lever which can select the bending direction of the first rod in response to the situation of employment by an operator is provided in the second rod. Due to this ligative suturer, the operator can regularly bend the first rod toward him whether he handles the suturer with his left or right hand.

13 Claims, 47 Drawing Sheets

ABDOMINAL OPERATION

CELIOSCOPIC OPERATION 5,662,666

LIGATIVE SUTURER

This application claims priority to Japanese Patent Application No. 7-294208, filed Nov. 13, 1995.

BACKGROUND OF THE INVENTION

1. Field of the Invention

The present invention relates to a ligative suturer, and more specifically, it relates to the structure of a ligative suturer which is employed for an endoscopic surgical operation.

2. Description of the Background Art

In general, an operation for surgically treating biliary calculus or pneumothorax is adapted to laparotomically incise a human body from the epigastrium to a portion around the umbilicus. However, such laparotomy results in a large wound, leading to a severe postoperative pain and requirement for hospitalization for 2 to 3 weeks. Further, the patient is forbidden to exercise hard for about 3 months after discharge.

In order to solve these problems, therefore, an endoscopic surgical operation is employed in recent years.

With reference to FIG. 29, such an endoscopic surgical operation is now described. In order to treat pneumothorax 403 which originates from a lung 402, for example, carbon dioxide ($CO_2$) is intraperitoneally supplied through a chest wall 400, to bring an abdominal cavity 401 into a positive pressure state. Thereafter the chest wall 400 is pushed up from its interior. Thus, a space which is necessary for the endoscopic surgical operation can be ensured.

Then, prescribed appliances called trocars 500 are passed through prescribed positions of the chest wall 400 to insert a celioscope 600, a forceps 6 and a ligative suturer 1 through the trocars 500, for carrying out the operation while projecting an image obtained from the celioscope 600 on a monitor (see FIG. 30).

When a patient 410 undergoes an abdominal operation, a wound 411 is formed between the epigastrium and a portion around the umbilicus, as shown in FIG. 31. If the patient 410 alternatively undergoes the aforementioned endoscopic surgical operation, however, only holes 412A to 412D are formed for inserting the trocars 500, as shown in FIG. 32.

Consequently, only hospitalization for 3 to 7 days is required, and the patient can orally ingest food from the day following the operation and gets better soon. Thus, the burden on the patient can be eased.

A ligation apparatus for ligating blood vessels which is employed for the endoscopic surgical operation is now described with reference to FIGS. 33 to 36, on the basis of a technique disclosed in Japanese Patent Laying-Open No. 7-51274 (1995).

In this ligation apparatus, a notched surface $1a$ is formed on a forward end of a rod 1 which consists of a metal rod having a diameter of about 4 mm or the like. A relatively heavy pillow-shaped movable body 2 is placed on the notched surface $1a$.

The movable body 2 is movably held by the notched surface $1a$ and a cover 3, while defining a space which is substantially similar to the diameter of a ligature 5. The cover 3 is fixed to the rod 1 by a screw 7. An angular thread guard 4 is formed on a prescribed position of the upper surface of the cover 3.

Further, the cover 3 is provided on its forward end with a ligature guide surface 3A consisting of a first slope 3 which is gradually inclined from the forward end toward the interior and a second slope $3e$ which downwardly extends to form a sharp angle with the first slope $3a$. A notched groove $3b$ is formed on the ligature guide surface 3A.

The movable body 2 has a trunk part $2c$ and a tapered end $2a$ which is provided on the forward end of the body part $2c$. The tapered end $2a$ is provided on its forward end with a hole $2b$ for fastening the ligature 5. On the other hand, a notched groove $1b$ is formed on the forward end of the notched surface $1a$.

The movable body 2 is supported by the notched surface $1a$ and the cover 3 so that the tapered end $2a$ forwardly protrudes from the notched grooves $3b$ and $1b$ which are formed in the central forward end of the ligature guide surface $3a$ and the forward end of the notched surface $1a$ respectively, as shown in FIGS. 35 and 36.

The movable body 2 is movably held in a space which is defined by the notched surface $1a$ and the cover 3, not to jut out from this space. This movable body 2 is so sized that the same has a clearance which is similar to the diameter of the ligature 5 in the space enclosed with the notched surface $1a$, the cover 3 and both side edges $3c$ of the cover 3 and is slightly moved following movement of the ligature 5.

A state of employment of the ligation appratus having the aforementioned structure is now described with reference to FIGS. 37 to 58 and FIGS. 59 to 66. FIGS. 59 to 66 are model diagrams for illustrating ligation in the ligation appratus.

Referring to FIG. 37, a second end of the ligature 5 whose first end is fastened to the tapered end $2a$ of the movable body 2 of the ligation apparatus is passed through the rear side of a blood vessel 10, so that this second end is grasped by a forceps 6. This state corresponds to that shown in FIG. 59.

Referring to FIG. 38, the ligature 5 is hung on the thread guard 4 which is provided on the upper side of the ligation apparatus, and bent along the blood vessel 10, to form an elongated ring. This state corresponds to that shown in FIG. 60.

Referring to FIG. 39, the ligature 5 is guided along the side edge of the cover 3 and slid on the ligature guide surface 3A, so that its intermediate portion is introduced into the interior of the cover 3 from the upper surface of the tapered end $2a$ of the movable body 2, as shown in FIG. 40. This state corresponds to that shown in FIG. 61.

Referring to FIGS. 41 to 45, the ligature 5 is moved in the space between the inner surface of the cover 3 and the upper surface of the movable body 2 and slid along the upper surface of the movable body 2, to be positioned on the notched surface $1a$ on the rear portion of the movable body 2. In the aforementioned respective operations, the tapered end $2a$ of the movable body 2 is supported by the notched grooves $3b$ and $1b$ of the cover 3 and the notched surface $1a$, while the movement of the rear side of the movable body 2 is limited on the inner surface of the side edge $3c$ of the cover 3. Thus, the movable body 2 inhibited from falling or the like. This state corresponds to that shown in FIG. 62.

Referring to FIGS. 46 to 49, the ligature 5 is advanced by the forceps 6 while being slid between the upper surface of the notched surface $1a$ and the lower surface of the movable body 2. This state corresponds to that shown in FIG. 63.

Referring to FIG. 50, the ligature 5 is pulled out from the notched surface $1a$, to be released from the thread guard 4. This state corresponds to that shown in FIG. 64. Thereafter the ligature 5 is pulled out from the notched surface $1a$ by the forceps 6, thereby forming a loop $5b$ having a twisted portion 5a defining a knot as shown in FIG. 51. This state corresponds to that shown in FIG. 65.

Referring to FIGS. 52 and 53, the ligature 5 is pulled along arrow to reduce the loop 5b, thereby forming a single knot 5c binding a portion around an affected part 10. This state corresponds to that shown in FIG. 66.

In order to prevent the single knot 5c from getting loose, the second end of the ligature 5 is returned by the forceps 6 so that the ligature 5 is hung on the thread guard 4 again for forming an elongated ring similarly to the above, thereby forming a new knot on the single knot 5c through a process similar to the above, as shown in FIGS. 54 to 58. Thus, a ligation part 5b is formed by a double knot which is not readily untied by external force.

Consequently, it is possible to readily ligate the blood vessel 10 in the abdominal cavity while observing a monitor, due to the ligation apparatus having the movable body 2 which is provided on the forward end of the rod 1.

In the aforementioned ligation apparatus, however, the thread guard 4 regularly protrudes from the upper surface of the cover 3. Therefore, it is rather difficult for the operator to release the ligature 5 from the thread guard 4 in the narrow abdominal cavity (see FIGS. 49 and 50). When the ligation apparatus is introduced into/discharged from the abdominal cavity with a trocar, further, the thread guard 4 may hang on the trocar to break the same.

According to the structure of the aforementioned ligation apparatus, further, the first end of the ligature 5 must be previously connected to the tapered end 2a of the movable body 2. Thus, the aforementioned ligation apparatus cannot be applied to an operation for blocking pneumothorax with an operative thread having needles mounted on both ends thereof.

SUMMARY OF THE INVENTION

An object of the present invention is to provide a ligative suturer, which can readily ligate a blood vessel and suture an opening in an endoscopic surgical operation.

In the ligative suturer according to the present invention, a rod comprises a first rod which is connected with a ligative sutural member and a second rod which is horizontally bendably connected with the first rod. The first rod is provided with a first rod member which is connected with the ligative sutural member on its forward end, and a first connection block which is provided to protrude from the rear end of the first rod member with a diameter smaller than that of the first rod member and has a first connection part connected with the second rod on its rear end.

Further, the second rod is provided with a second rod member which is provided to be movable along the axial direction of the rod and capable of storing the first connection block protruding from the first rod member on its forward end, and has a first grip member on its rear end, a third rod member which is stored in the second rod member for guiding movement of the second rod member in the axial direction of the rod on its outer peripheral surface and has a flange part on its rear end in a region which is exposed from the second rod member, a first elastic member which is provided on the outer peripheral surface of the third rod member between the first grip member and the flange part of the third rod member for regularly urging the second rod member toward the forward end, stores the first connection block and brings the same into contact with the rear end of the first rod member, a fourth rod member having a forward end which is stored in the rear end of the second rod member, a lever member having an end which is pivotally supported on the forward end side to be horizontally movable, and a second grip member which is provided on its rear end, a second elastic member which is provided on the outer peripheral surface of the fourth rod member between the flange part of the third rod member and the second grip member for urging the fourth rod member toward the rear end with elastic force which is larger than that of the first elastic member, first and second slide members having first and second slide blocks which are stored in the third rod member on portions closer to the forward end than the lever member for horizontally holding the first connection part and forwardly pushed by the lever member following movement of the fourth grip member toward the forward end, and first and second contact bars which are provided on the forward ends of the first and second slide blocks respectively to be in contact with the first connection block, a second connection block which is stored in the forward end of the third rod member and has a second connection part which is horizontally movably connected with the first connection part and first and second guide passages storing the first and second contact bars therein for guiding sliding of the first and second contact bars on its forward end, and a third elastic member which is provided on the outer peripheral surfaces of the first and second contact bars between the first and second slide blocks and the second connection block for regularly urging the first and second slide members toward the rear ends.

When the first and second grip members are grasped in the ligative suturer having the aforementioned structure, only the second rod member is first moved toward the rear end with respect to the third rod member due to the relation in elastic force between the first and second elastic members, to open the connection parts of the first and second connection blocks.

Due to the grasp of the first and second grip members, further, the fourth rod member is moved toward the forward end with respect to the third rod member. Following this, the first or second slide member is moved toward the forward end so that the first or second contact bar comes into contact with the first connection block by the lever member, and the overall first rod is bent about the first connection part.

If the ligative suturer is handled with a right hand at this time, for example, the lever member rightwardly falls along the rightward gravitational direction in general, to move the first slide member provided on the right side toward the forward end, whereby the first rod is leftwardly bent toward the operator. Consequently, the operator can readily perform a ligative sutural operation.

If the ligative suturer is handled with a left hand, on the other hand, the lever member is leftwardly inclined along the leftward gravitational direction in general, whereby the first rod is rightwardly bent as the result. Also in this case, therefore, the first rod is inclined toward the operator, to facilitate a ligative sutural operation.

Preferably, a thread guard is provided on the upper surface of the first rod for hanging the operative thread thereon for arranging the intermediate portion of the operative thread on the upper side of the rod, and this thread guard is provided with a thread guard member which is provided in the first rod and rotated about a central axis provided on the first connection block, for enabling protrusion and storage, a forwardly movable working bar which is stored along guide grooves horizontally provided to hold the first connection block to be pushed by the first or second contact bar toward the forward end following the forward movement of the first or second contact bar, an engaging pin which is provided on the working pin to engage with the thread guard member so that the thread guard member protrudes following forward movement of the working bar, and stores the thread guard member following rearward movement of the working bar, and a fourth elastic member which is provided between the forward end of the first rod member and the working bar for regularly urging the working bar toward the rear end.

According to this structure, it is possible to allow protrusion of the thread guard while grasping the first and second grip members for bending the overall first rod in a prescribed direction. Further, the thread guard can be stored by weakening the force for grasping the first and second grip members.

Consequently, an operative thread which is hung on the thread guard in the narrow abdominal cavity can be readily released in an endoscopic surgical operation, whereby the burden on the operator can be reduced. Further, a trocar etc. can be prevented from damage caused by the thread guard member.

Further, the first and second grip members are provided with a locking mechanism for maintaining the first and second grip members in stationary states against urging force of the first and second elastic members. Thus, the bent state of the first rod can be maintained with no grasping force of the operator, whereby the burden on the operator can further be reduced.

Preferably, the first rod has an outwardly inclined surface so that a surface of the first rod to be in contact with the second rod comes into contact with the second rod in a most bent state of the first rod, and a member having a large coefficient of friction is mounted on a surface of the second rod to be in contact with the first rod.

Thus, the operative thread can be held at the bent portions of the first and second rods, whereby the operator can readily perform a ligative sutural operation.

Further, only the thread support part is provided to be different in color from the remaining elements. Thus, the operator can clearly recognize the thread support part when he hangs the operative thread on the thread support part while observing the monitor. Consequently, the burden on the operator can be reduced in the ligative sutural operation.

Preferably, the ligative sutural member is detachably provided on the forward end of the first rod. In order to enable such detachable provision, the ligative sutural member is provided with a neck portion which is provided on the rear end of the body part and has a smaller diameter than the body part, and first and second convex parts which have different widths and are provided around the neck portion on positions outwardly opposite to each other, and the first rod is provided on its forward end with an opening which is defined by a flange part having first and second window parts in positions corresponding to the first and second convex parts respectively for receiving the neck portion provided on the body part, a contact plate which is provided in the first rod for blocking the opening provided in the forward end of the first rod, and a fifth elastic member for urging the contact plate toward the forward end of the first rod.

Therefore, the ligative sutural member can be fixed to the rod by aligning the first and second convex parts which are provided on the ligative sutural member with the first and second window parts provided on the rod, inserting the neck portion of the ligative sutural member in the rod while pushing the contact plate toward the rear end, and rotating the ligative sutural member in this state.

Thus, it is possible to select a ligative sutural member which is suitable for the thickness of the operative thread by bringing the ligative sutural member into the structure detachable on the forward end of the rod, whereby generality of the ligative suturer can be improved.

Preferably, the fourth and fifth elastic members are formed by the same member. Thus, the first rod of the ligative suturer can be reduced in length.

Preferably, the body part is provided with an upper convex part which is formed on the upper surface to downwardly extend from the forward end toward the rear end, a lower convex part which is provided on the lower surface to be continuous with the upper convex part at a prescribed space, and a space part which is defined in the rear end by the upper and lower convex parts, and the movable body has a substantially circular thread support part which is provided on its forward end and has a notched portion extending toward the forward end on its rear side, and a support hole which is provided on its rear end for receiving the upper and lower convex parts with a prescribed space.

Due to employment of the ligative sutural member having the aforementioned structure, the operative thread can be readily induced from the upper surface toward the lower surface of the movable body since the opening for passing the operative thread therethrough is larger than that in the conventional one.

Further, a substantially circular support part having a forwardly extending notched portion on its rear side is provided on the forward end of the movable body, whereby the operative thread can be supported by the thread support part by simply hanging the operative thread on the notched portion while winding the same on the thread support part. Thus, the ligative suturer can be further improved in operability.

In addition, operability of the operative thread can be improved by providing the thread support part to be downward beyond the support hole toward the front end.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS (Embodiment 1)

A ligative suturer 20 according to an embodiment 1 of the present invention is now described with reference to the drawings. In the ligative suturer 20 according to the embodiment 1, a thread guard 4 is stored in the interior of a rod by a manual operation.

Figure 1:
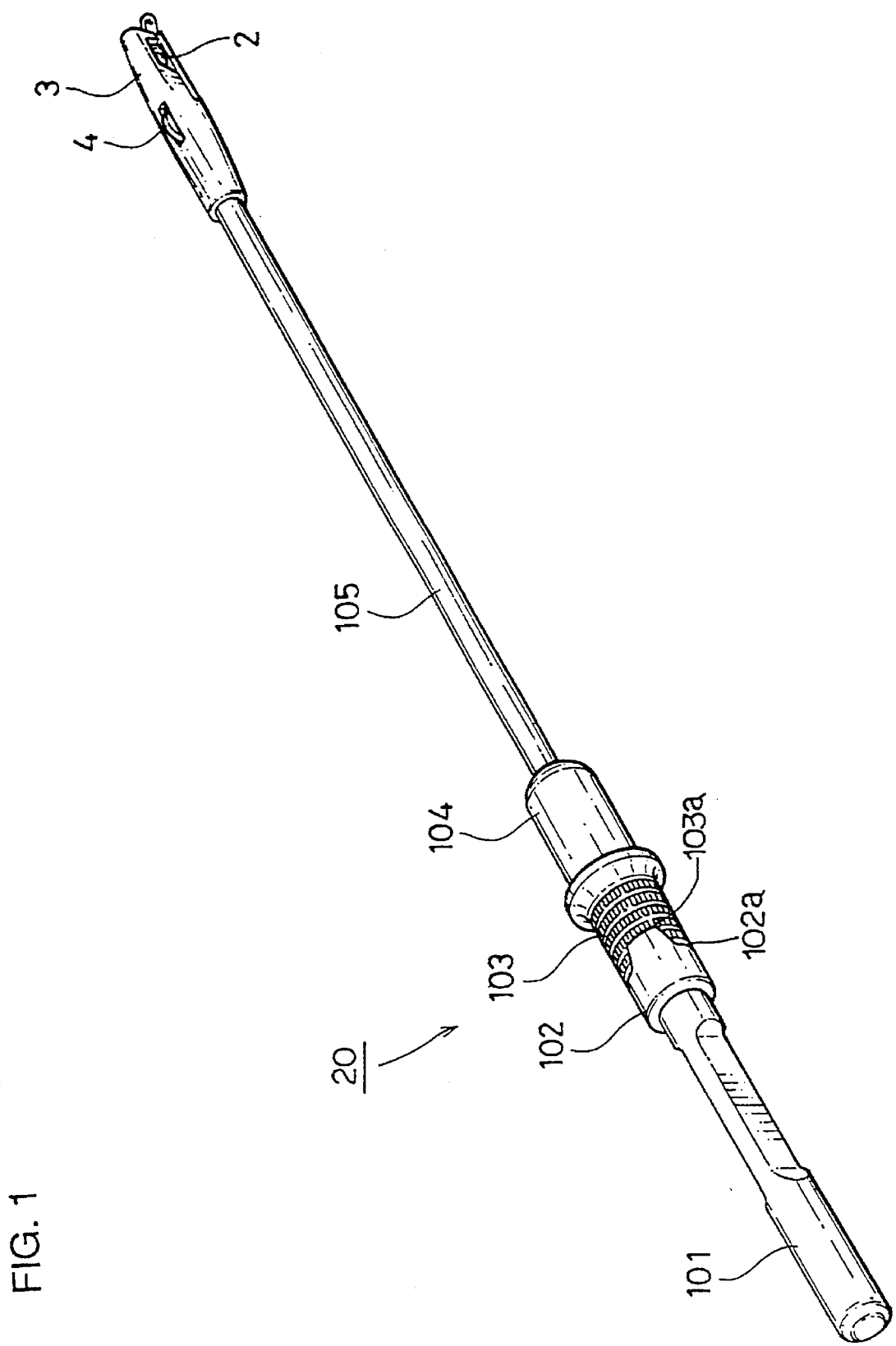
FIG. 1 is a perspective view showing the appearance of a ligative suturer according to an embodiment 1 of the present invention.

With reference to FIG. 1, the structure of the ligative suturer 20 is now schematically described.

A grip 101 is provided with fixed and rotatable knobs and 103 having irregular surfaces 102a and 103a corresponding to each other respectively.

Figure 33:
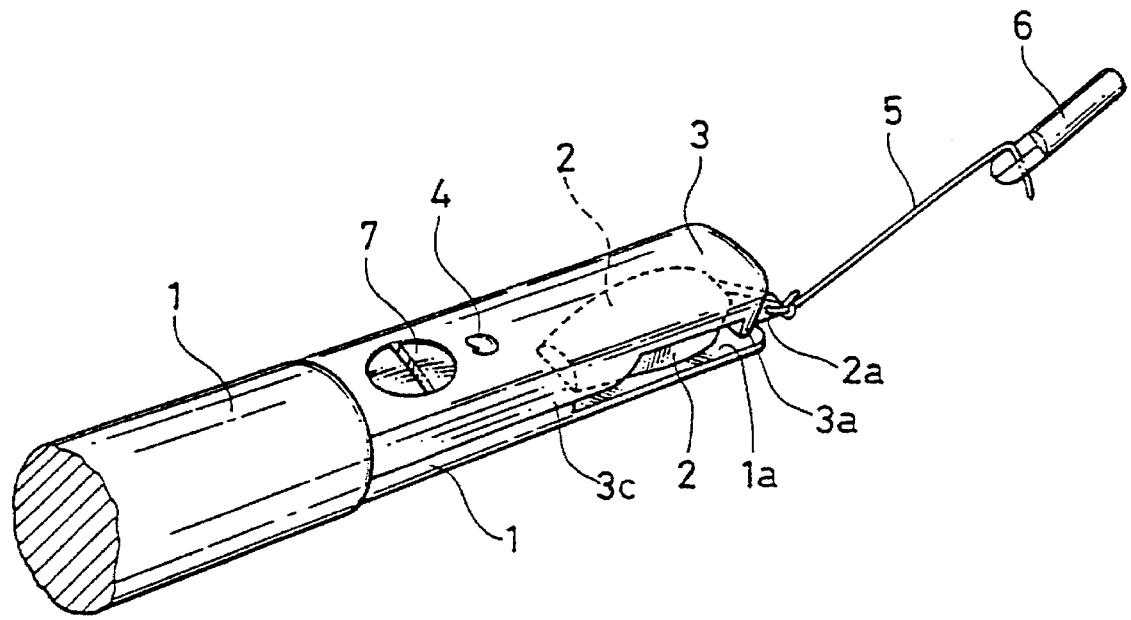
FIG. 33 is a perspective view showing the structure of a ligation apparatus according to the prior art.
Figure 34:
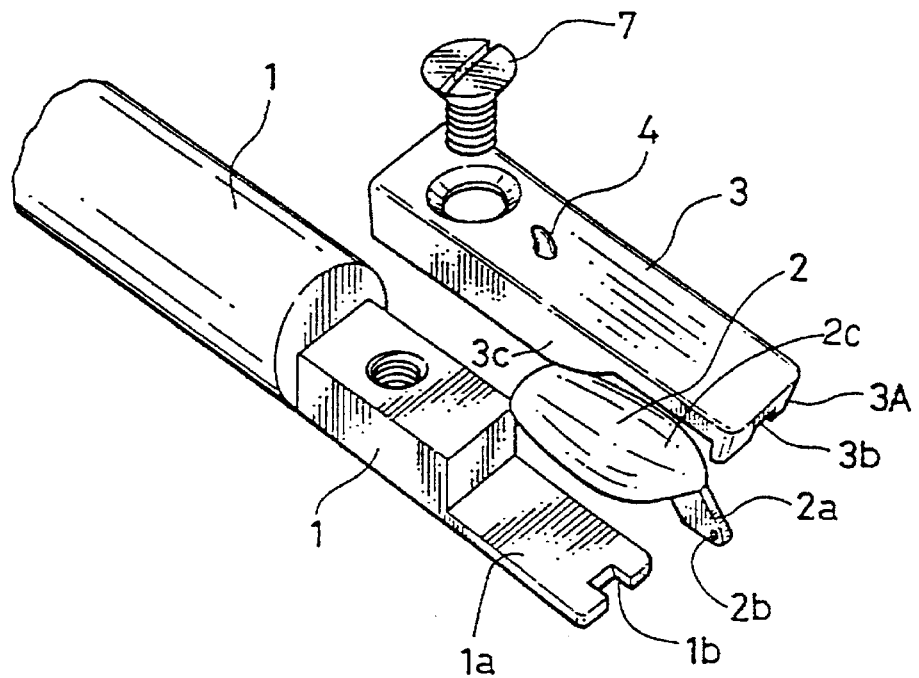
FIG. 34 is an exploded perspective view of the ligation apparatus shown in FIG. 33.
Figure 35:
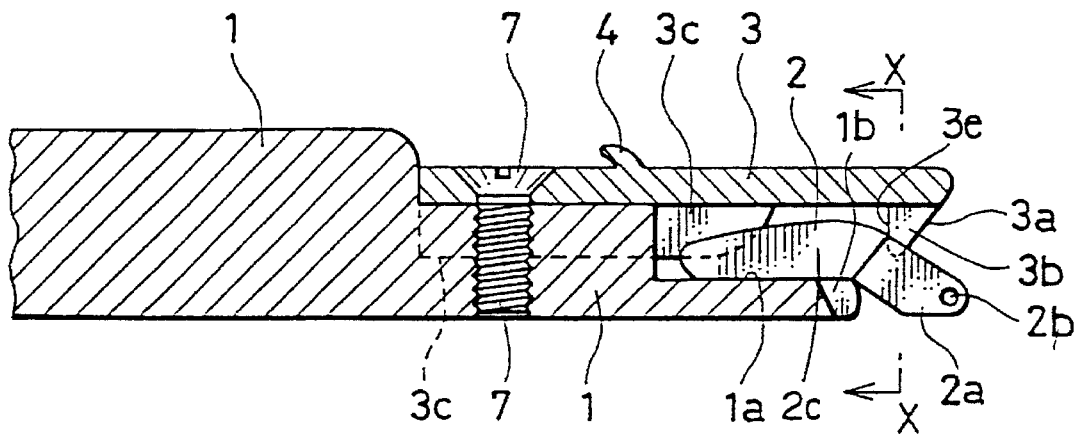
FIG. 35 is a sectional view of the ligation apparatus shown in FIG. 33 taken along its axial direction.
Figure 36:
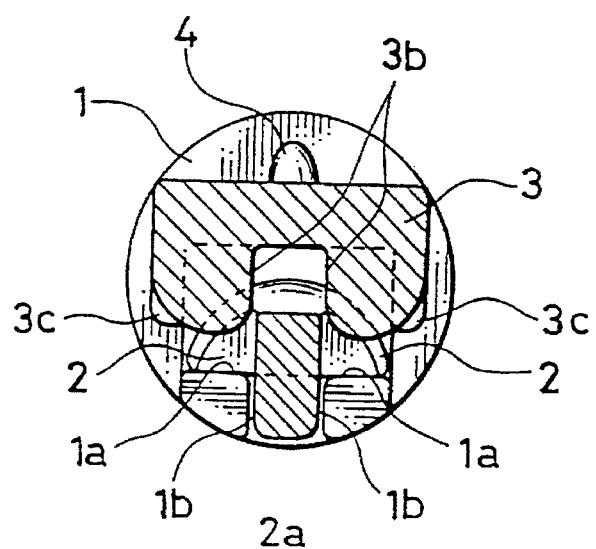
FIG. 36 is a sectional view taken along the line X—X in FIG. 35.

A cover 104 is provided on an upper portion of the rotatable knob 103, so that a rod 105 extends from the forward end of the cover 104 and a ligative suturer having a structure which is similar to that of the prior art described with reference to FIG. 33 is mounted on the forward end of the rod 105.

The internal structure of the ligative suturer 20 is now described with reference to FIGS. 2 and 3. The thread guard 4 is provided in the rod 105 to be rotatable about a central axis 4a. In the state shown in FIG. 2, the thread guard 4 is stored.

The rod 105 is provided therein with a working shaft 107a which is movable along the axial direction of the rod 105 so that its forward end is rotatably mounted on the thread guard 4 by a shaft 4b. The working shaft 107a is horizontally moved along the axial direction of the rod 105, thereby rotating the thread guard 4 about the axis 4a.

A spring 108 is mounted on the rear end of the working shaft 107a, for urging the working shaft 107a to be arranged on the rear end of the rod 105.

The fixed knob 102 is fixed to the grip 101 through a machine screw 102A. On the other hand, the rotatable knob 103 is rotatably mounted on the grip 101. The cover 104 is fixed to the working shaft 107a through a machine screw 106A, and a slot 105b is provided in the outer peripheral surface of the rod 105 so that the cover 104 is slidable along the rod 105.

When the rotatable knob 103 is rotated along the outer peripheral surface of the grip 101 in the aforementioned structure, the rotatable knob 103 is pushed up toward the forward end due to the engagement of the irregular surfaces 102a and 103a which are provided on the fixed and rotatable knobs 102 and 103 respectively. Thus, the cover 104 is also pushed up along with the rotatable knob 103.

At this time, the working shaft 107a is moved toward the forward end against the urging force of the spring 108, since the cover 104 is fixed to the working shaft 107a by the machine screw 106A. Thus, the thread guard 4 is rotated about the axis 4a along arrow as shown in FIG. 3, thereby protruding from the surface of the rod 105.

Figure 2:
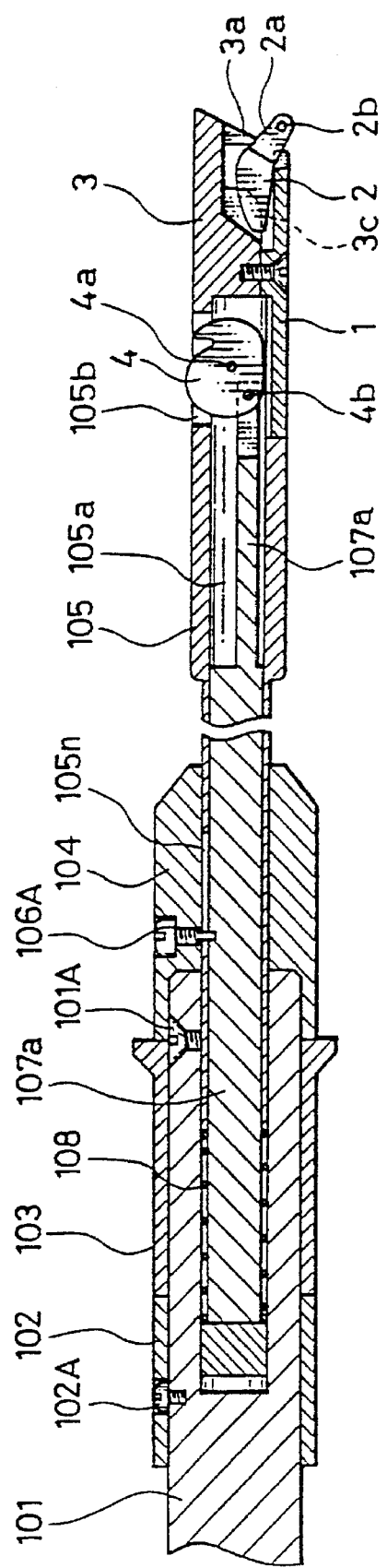
FIGS. 2 and 3 are first and second sectional views showing the structure of the ligative suturer according to the embodiment 1 of the present invention.
Figure 3:
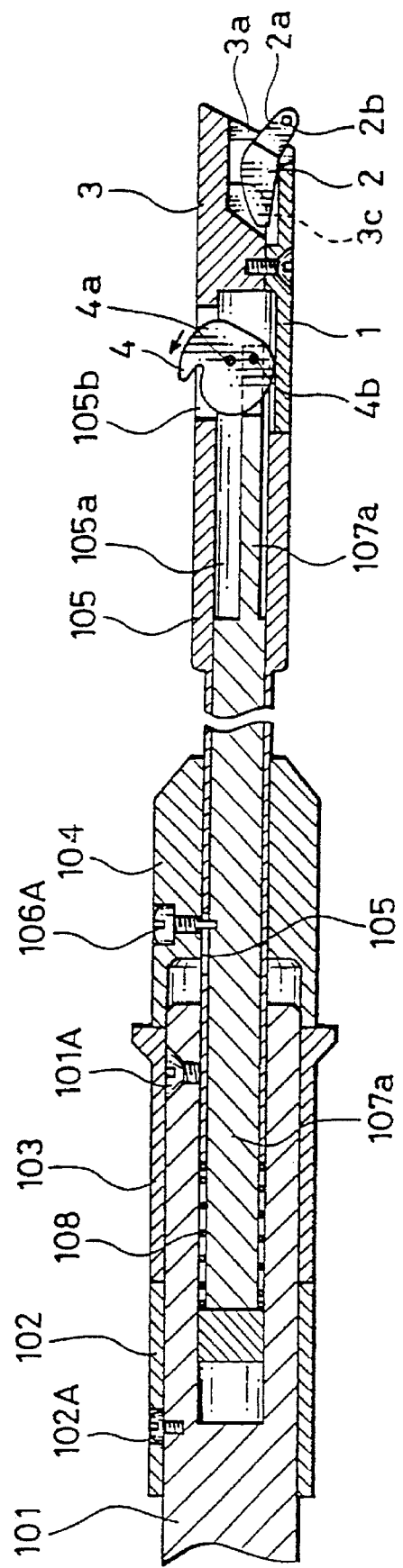

When the rotatable knob 103 is further rotated, the working shaft 107a, which is regularly subjected to force for returning the same toward the rear end, is to be immediately returned to the state shown in FIG. 2.

When the ligative suturer 20 having the aforementioned structure is employed for an endoscopic surgical operation, therefore, a ligative operation can be efficiently performed in the endoscopic surgical operation since the thread guard 4 can be handled by a manual operation.

In the ligative suturer 20 according to this embodiment, the ligative operation on a portion to be ligated is identical to that described above with reference to FIGS. 37 to 66, and hence redundant description is omitted.

(Embodiment 2)

A ligative suturer according to an embodiment 2 of the present invention is now described.

Figure 4:
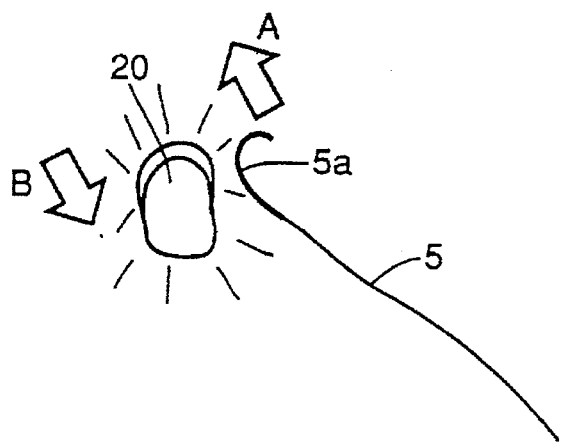
FIGS. 4 and 5 are first and second diagrams showing a sutural procedure with an operative thread.

When pneumothorax 20 is sutured in an endoscopic surgical operation as shown in FIG. 4, an operative thread 5 having an operative needle 5a only on one end thereof cannot be turned around the pneumothorax 20 along arrows A and B, since the intraperitoneal space is extremely limited.

Figure 5:
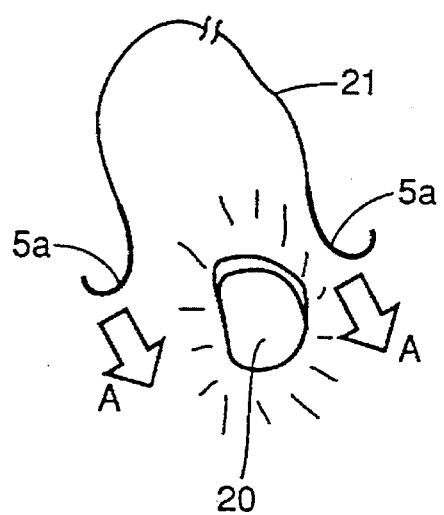

In an endoscopic surgical operation of such pneumothorax 20, therefore, an operative thread 21 having operative needles 5a on both ends thereof is employed for suturing the pneumothorax 20 in the same direction along arrows A, as shown in FIG. 5.

When the aforementioned ligative suturer 20 according to the embodiment 1 is employed for suturing an opening such as the pneumothorax 20 in the endoscopic surgical operation, it takes much time to temporarily take out the operative thread 5, since an end of the operative thread 5 must be previously connected to the forward end of the movable body 2. In relation to the embodiment 2, a ligative suturer 30 which enables a sutural operation of an opening in an endoscopic surgical operation of pneumothorax etc. is described.

Figure 6:
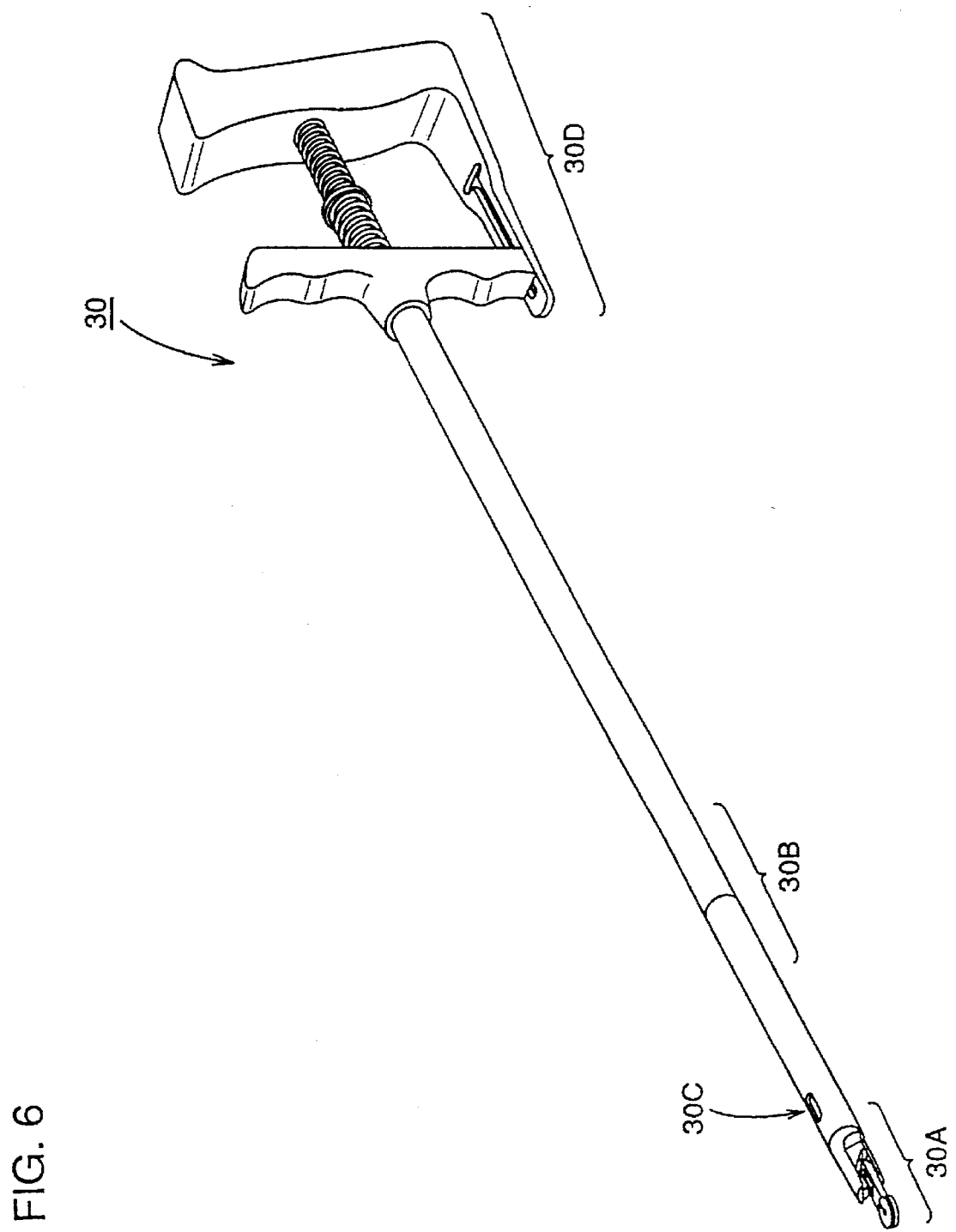
FIG. 6 is a perspective view showing the appearance of a ligative suturer according to an embodiment 2 of the present invention.

As shown in a general perspective view of FIG. 6, the ligative suturer 30 according to the embodiment 2 has a ligative sutural member 30A provided on its forward end, a thread guard 30C, a central bent portion 30B and a grip portion 30D.

Figure 7:
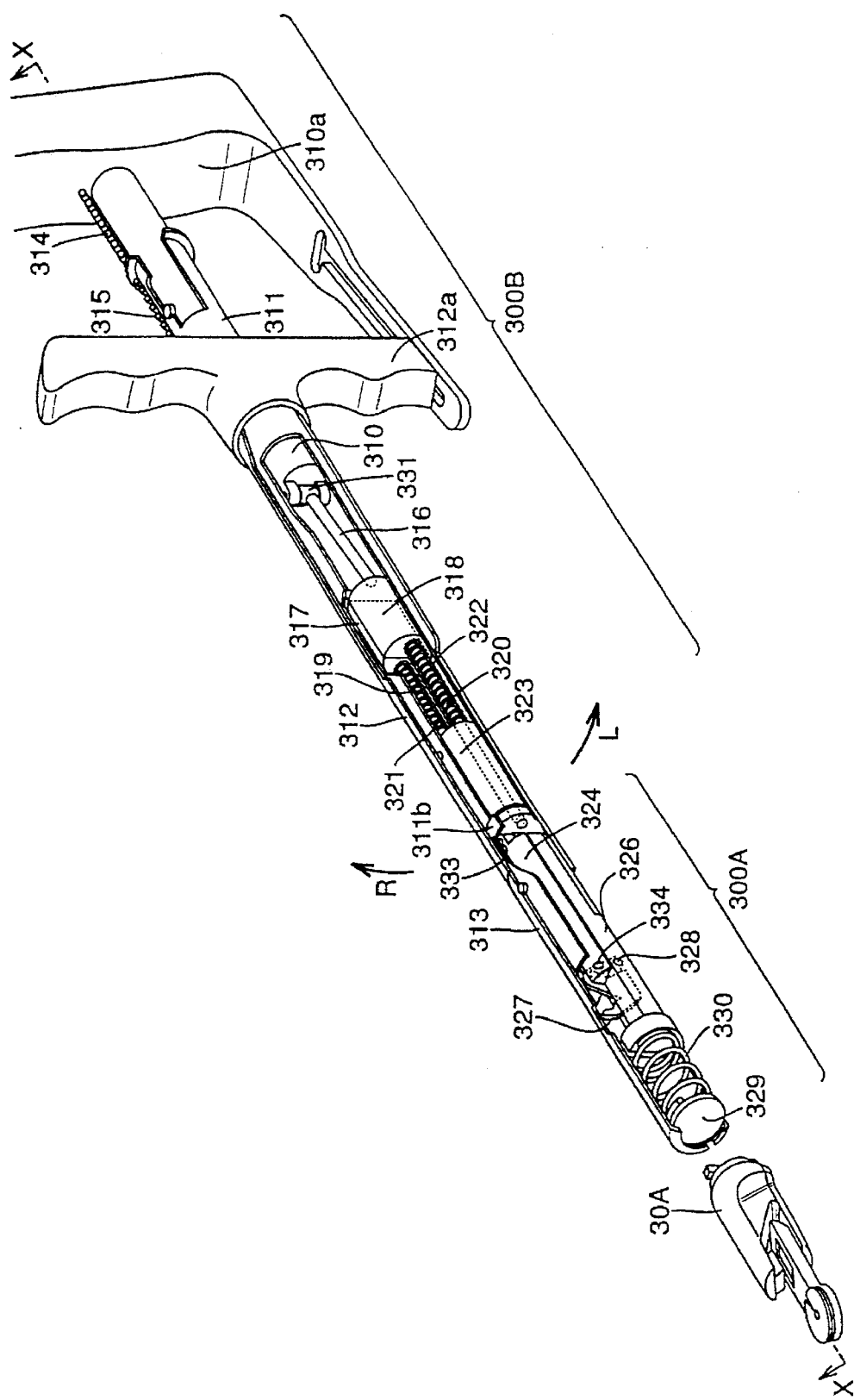
FIG. 7 is a perspective view showing the internal structure of the ligative suturer according to the embodiment 2 of the present invention.
Figure 8:
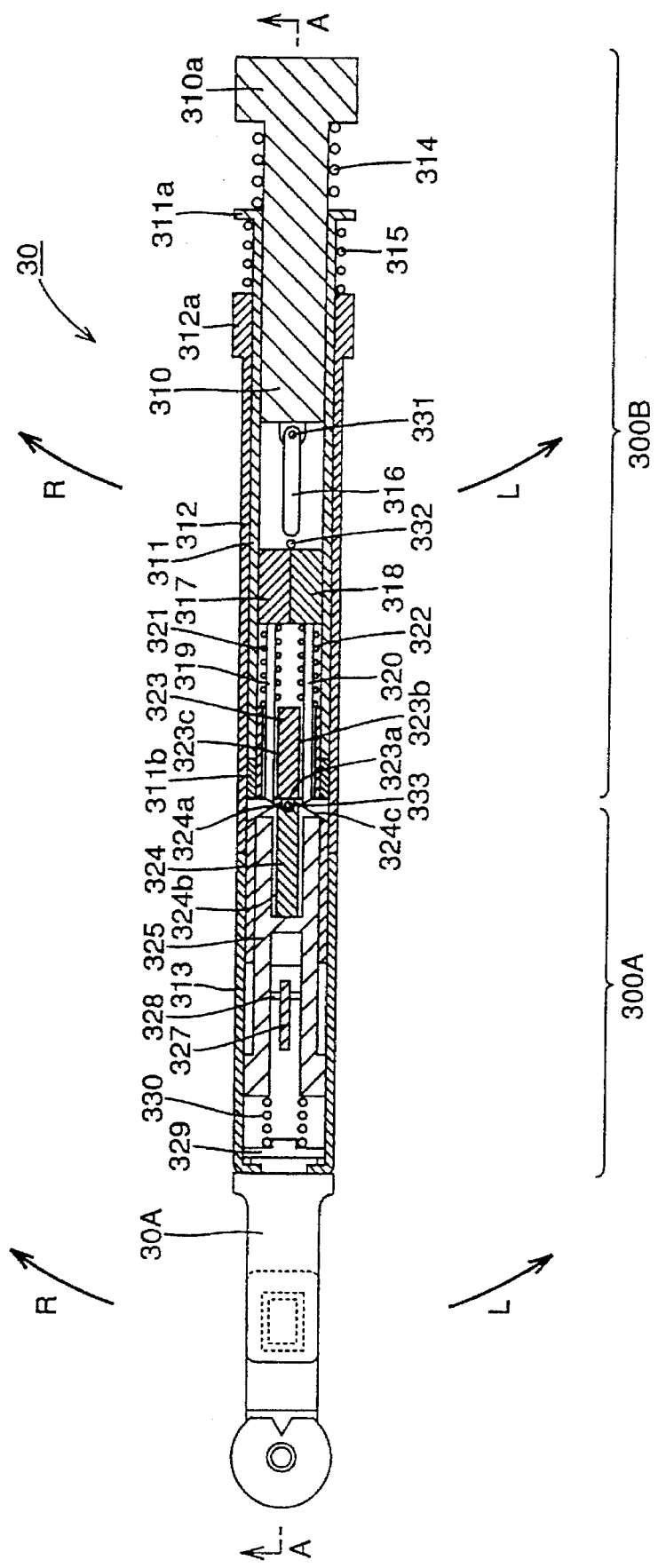
FIG. 8 is a sectional view taken along the line X—X in FIG. 7.
Figure 9:
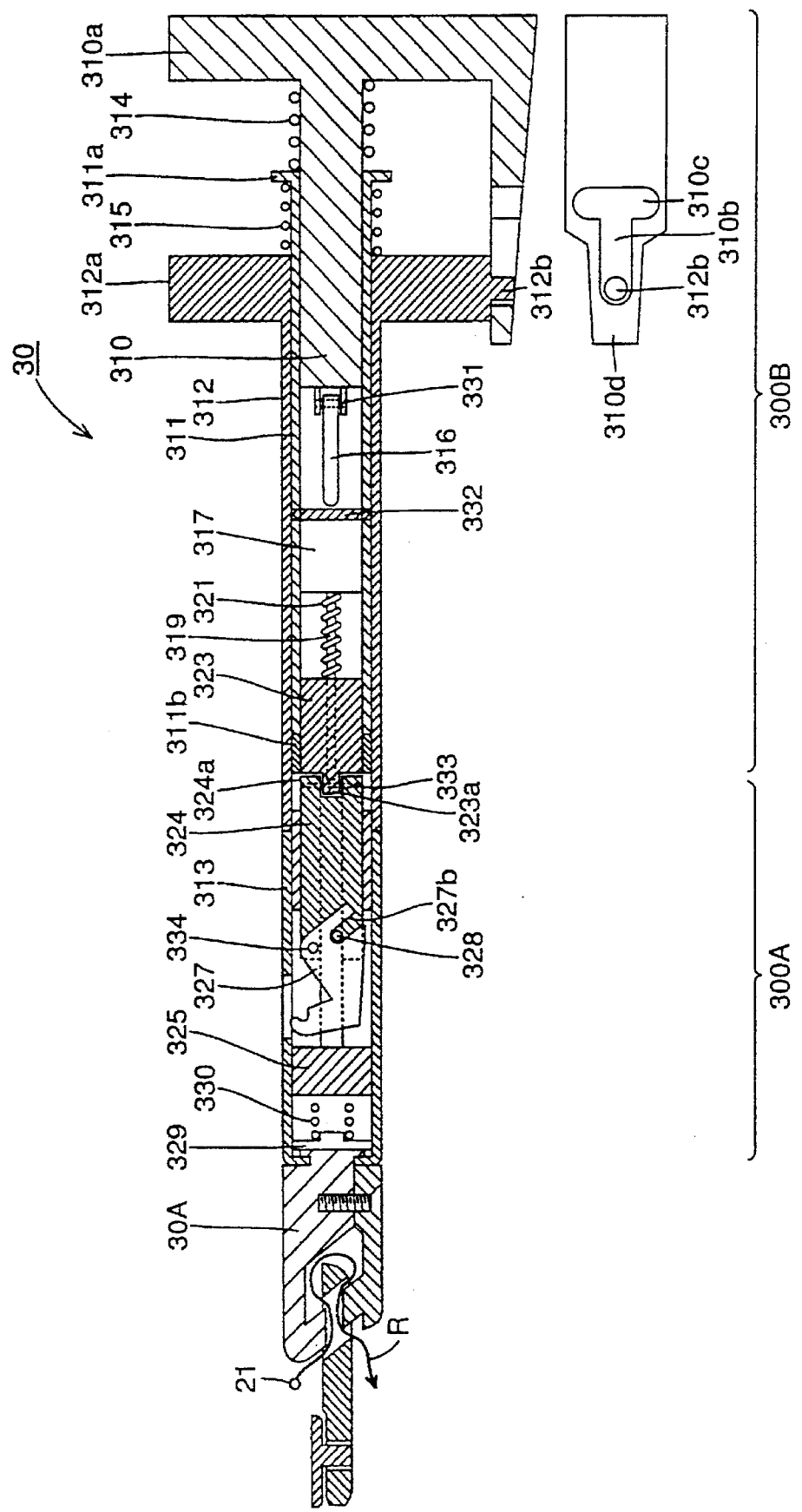
FIG. 9 is a sectional view taken along the line A—A in FIG. 8.

With reference to a partially fragmented perspective view of the ligative suturer 30 shown in FIG. 7 and sectional views shown in FIGS. 8 and 9, the internal structure of the ligative suturer 30 is now described. FIGS. 8 and 9 are sectional views taken along the lines X—X and A—A in FIGS. 7 and 8 respectively.

The ligative suturer 30 has a first rod 300A which is connected with the ligative sutural member 30A on its front end, and a second rod 300B. The first rod 300A is connected with the second rod 300B to be bendable along arrow R or L in the figures.

The first rod 300A is provided with a cylindrical first rod member 313 which is connected with the ligative sutural member 30A on its forward end. A contact plate 329 for fixing the ligative sutural member 30A and a spring 330 for urging the contact plate 329 toward the forward end are provided on the forward end portion of the first rod member 313.

On the other hand, a first connection block 324 is provided on the rear end of the first rod member 313, so that its rear end protrudes from the rear end portion of the first rod member 313 by a prescribed distance. A first connection part 324a is provided on the rear end of this first connection block 324.

The first connection block 324 is provided with a working bar 325 which is movable along the axial direction of the first rod member 313, to be guided into a guide passage 324b provided in the first connection block 324.

A thread guard member 327 is arranged in a prescribed space which is defined by the working bar 325. A rotation axis 334 of the thread guard member 327 is fixed to the first connection block 324, while an engaging pin 328 is mounted on the working bar 325, for engaging with an engaging groove 327b which is provided in the thread guard member 327.

The forward end portion of the working bar 325 is urged toward the rear end by a spring member 330 which urges the contact plate 329 toward the forward end.

The second rod 300B has a second rod member 312 which is axially movably provided to be capable of storing the first connection block 324 protruding from the first rod member 313 on its forward end, and provided with a first grip 312a on its rear end. The second rod member 312 is provided therein with a third rod member 311 for guiding axial movement of the second rod member 312 on its outer peripheral surface. A flange part 311a is formed on the rear end portion of the third rod member 311.

On the outer peripheral surface of the third rod member 311 between the first grip 312a and the flange part 311a, a first grip spring 315 is provided for regularly bringing the second rod member 312 into contact with the first rod member 313 and storing the first connection block 324 in the second rod member 312.

A fourth rod member 310 which is provided with a second grip 310a on its rear end is stored in the internal rear end of the third rod member 311. The fourth rod member 310 is provided on its forward end with a lever member 316 having an end which is pivotally supported by a pivotal part 331 to be rotatable along arrow R or L.

Further, a second grip spring 314 having stronger elastic force than the first grip spring 315 is provided on the outer surface of the fourth rod member 310 between the flange part 311a and the second grip 310a.

The elastic force of the first grip spring 315 is set at 0.03 kg/1 mm, while that of the second grip spring 314 is set at 0.1 kg/1 mm, for example.

First and second slide members 317 and 318 are stored in a portion of the third rod member 311 on the forward end of the lever member 316, while first and second contact bars 319 and 320 are mounted on the forward ends of the first slide members 317 and 318 respectively, to extend toward the forward end of the third rod member 311.

The forward end of the third rod member 311 stores a second connection block 323, which is provided with first and second contact bar guide passages 323c and 323b for guiding the first and second contact bars 319 and 320 respectively.

Further, a second connection part 323a is provided on the forward end of the second connection block 323, to be rotatably connected with the first connection part 324a of the first connection block 324 by a pivotal part 333.

First and second slide springs 321 and 322 are mounted on the first and second contact bars 319 and 320 which are provided between the first and second slide members 317 and 318 and the second connection block 323 respectively, for regularly supplying rearward urging force to the first and second slide members 317 and 318. Further, a locating pin 332 is provided for limiting the rearward movement of the first and second slide members 317 and 318.

The second grip 310a is provided with a guide surface 310d having a first groove 310b axially extending along the side surface of the first grip 312a and a second groove 310c communicating with the first groove 310b and extending perpendicularly thereto, while a locking bar 312b is provided on the side surface of the first grip 312, to engage in the first and second grooves 310b and 310c.

On the rear end portion of the first connection block 324, on the other hand, an outwardly inclined contact surface 324c is so provided that its surface to be in contact with the second rod 300B of the first connection block 324 comes into contact with the second rod 300B in a most bent state of the first rod 300A.

Further, the third rod member 311 is provided on its portion which is in contact with the contact surface 324c with a member, such as a rubber member 311b in this embodiment, for example, having a large coefficient of friction, for holding an operative thread in this portion.

Figure 10:
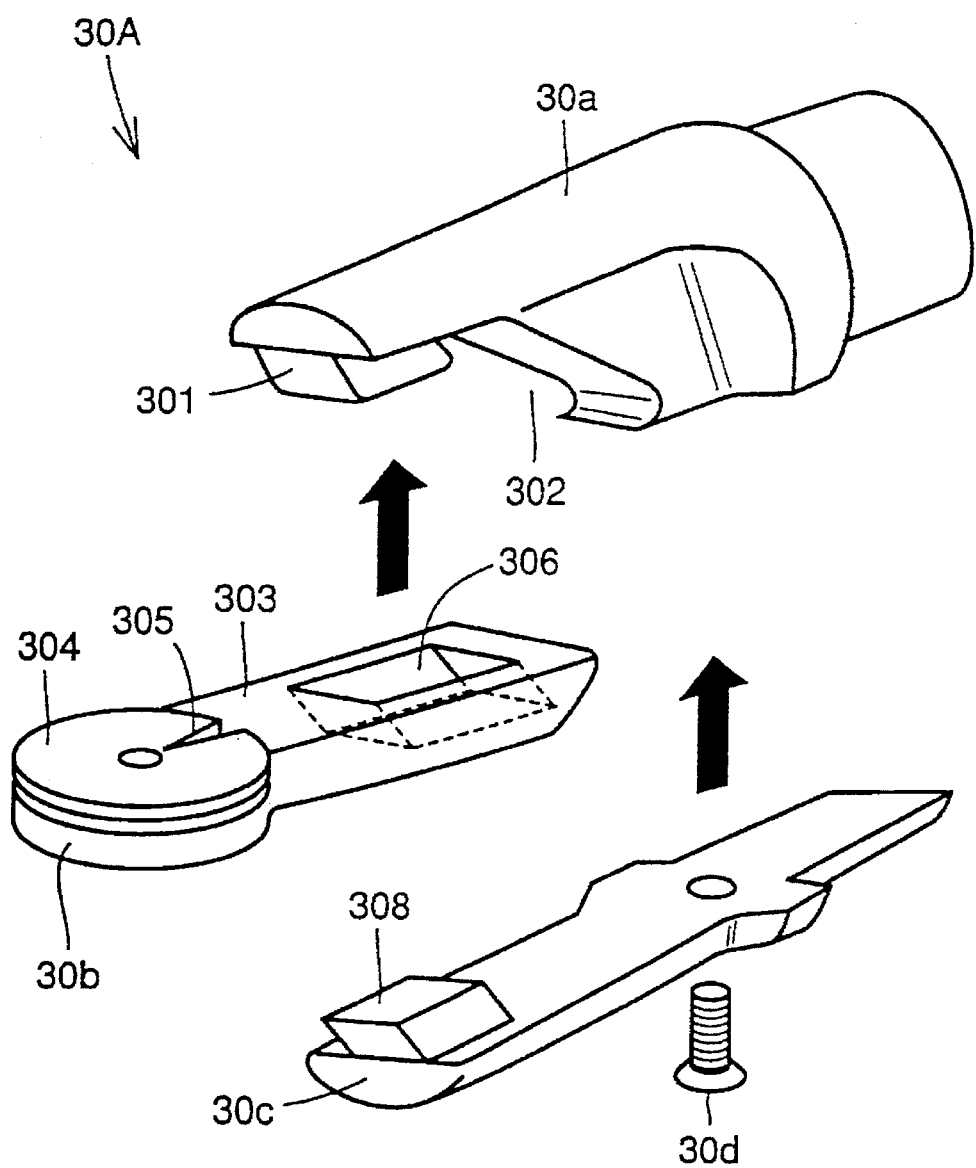
FIG. 10 is an exploded perspective view showing the structure of a ligative sutural member according to the embodiment 2 of the present invention.

With reference to FIG. 10, the structure of the ligative sutural member 30A according to this embodiment is now described.

This ligative sutural member 30A has vertically divided first and second body parts 30a and 30c. The first body part 30a is provided on its forward end portion with a downwardly extending upper convex part 301 and an opening 302 which is integrally formed with the second body part 30c behind the upper convex part 301.

On the other hand, the second body part 30c is provided on its forward end portion with a lower convex part 308 which is formed to be continuous with the upper convex part 301 provided on the forward end portion of the first body part 30a at a prescribed distance. The first and second body parts 30a and 30c are fixed to each other by a screw 30d.

A movable body 30b has a trunk part 303 and a substantially circular thread support part 304 which is mounted on the forward end of the trunk part 303. A forwardly extending notched portion 305 is formed on the rear end of the thread support part 304. On the other hand, the trunk part 303 is provided on its rear end with a support hole 306, so that the upper and lower convex parts 301 and 308 of the first and second body parts 30a and 30c engage therein at a prescribed space. In the ligative sutural member 30A having the aforementioned structure, an operative thread 21 is passed through a route shown by arrow R in the sectional structure of FIG. 9.

Figure 11:
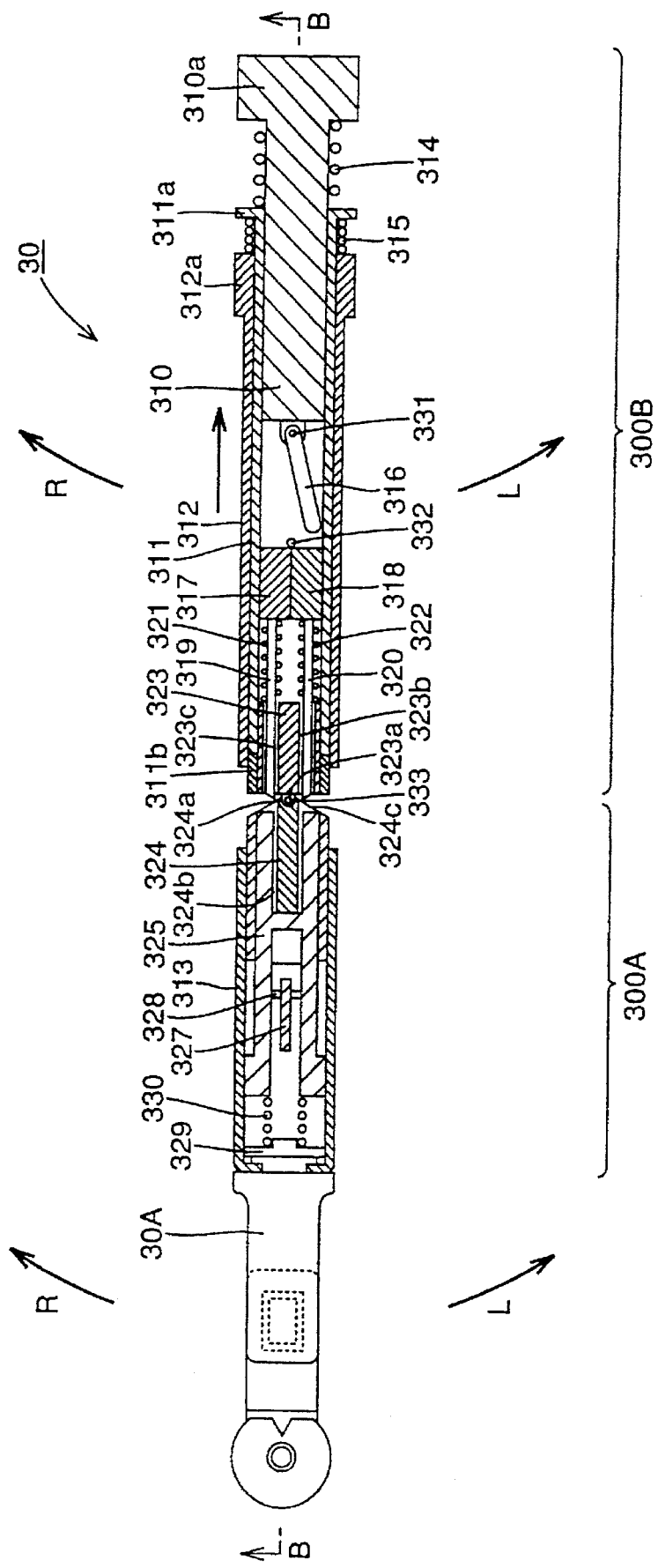
FIG. 11 is a first sectional view showing the operation of the ligative suturer according to the embodiment 2 of the present invention.
Figure 12:
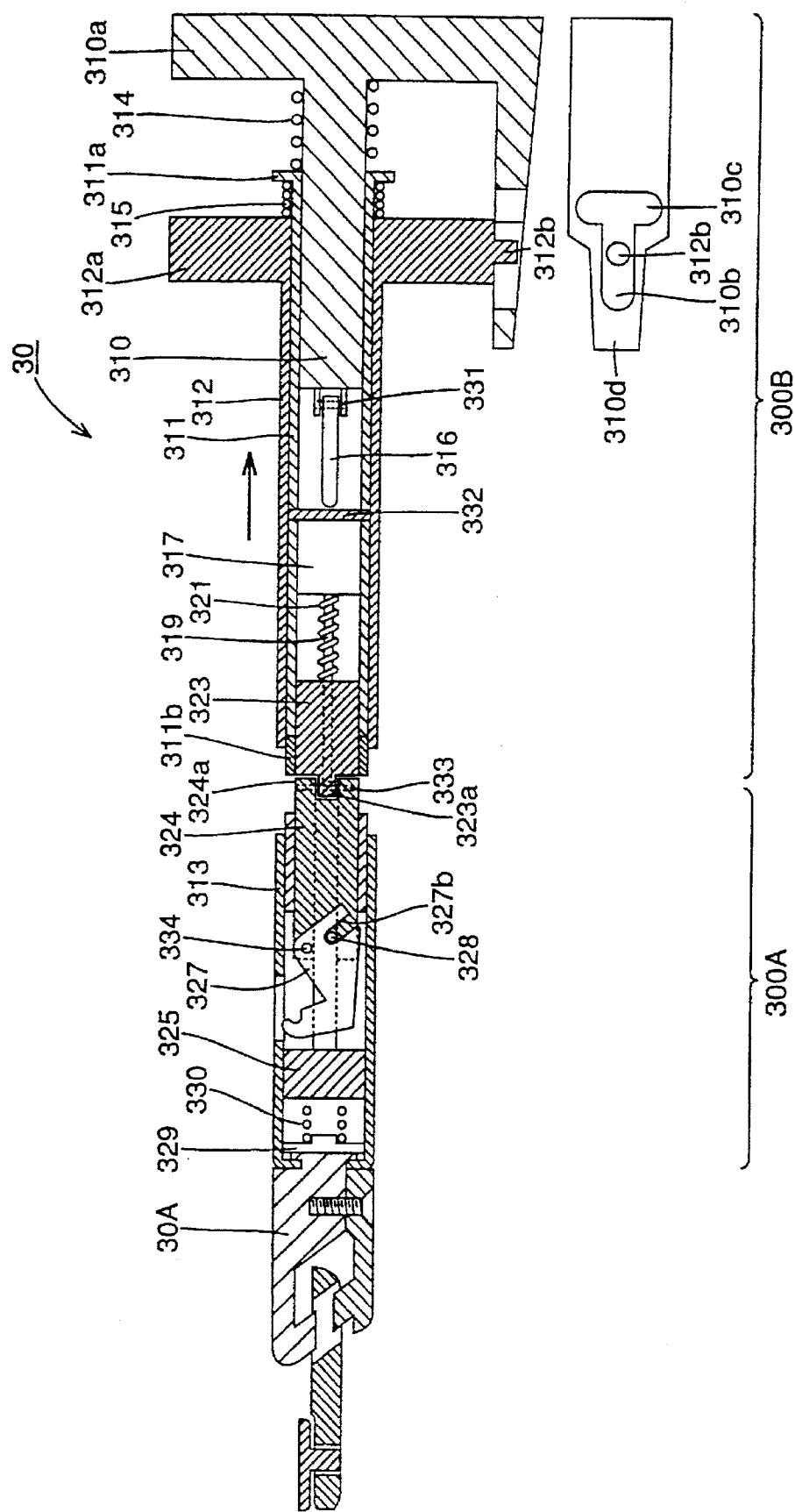
FIG. 12 is a sectional view taken along the line B—B in FIG. 11.

The operation principle of the aforementioned ligative suturer 30 is now described with reference to FIGS. 11 to 14. FIGS. 11 and 12 are sectional views taken along the lines X—X and B—B in FIGS. 7 and 11 respectively, while FIGS. 13 and 14 are sectional views taken along the lines X—X and C—C in FIGS. 7 and 13 respectively.

Referring to FIGS. 11 and 12, the first and second grips 312a and 310a are tightly grasped so that the first grip spring 315 is first compressed due to the relation in elastic force between the first and second grip springs 315 and 314 and only the second rod member 312 is rearwardly moved with respect to the third rod member 311, thereby opening the connection part between the first and second connection blocks 324 and 323. It is assumed that the lever member 316 is rotated along arrow L at this time, for example.

Figure 13:
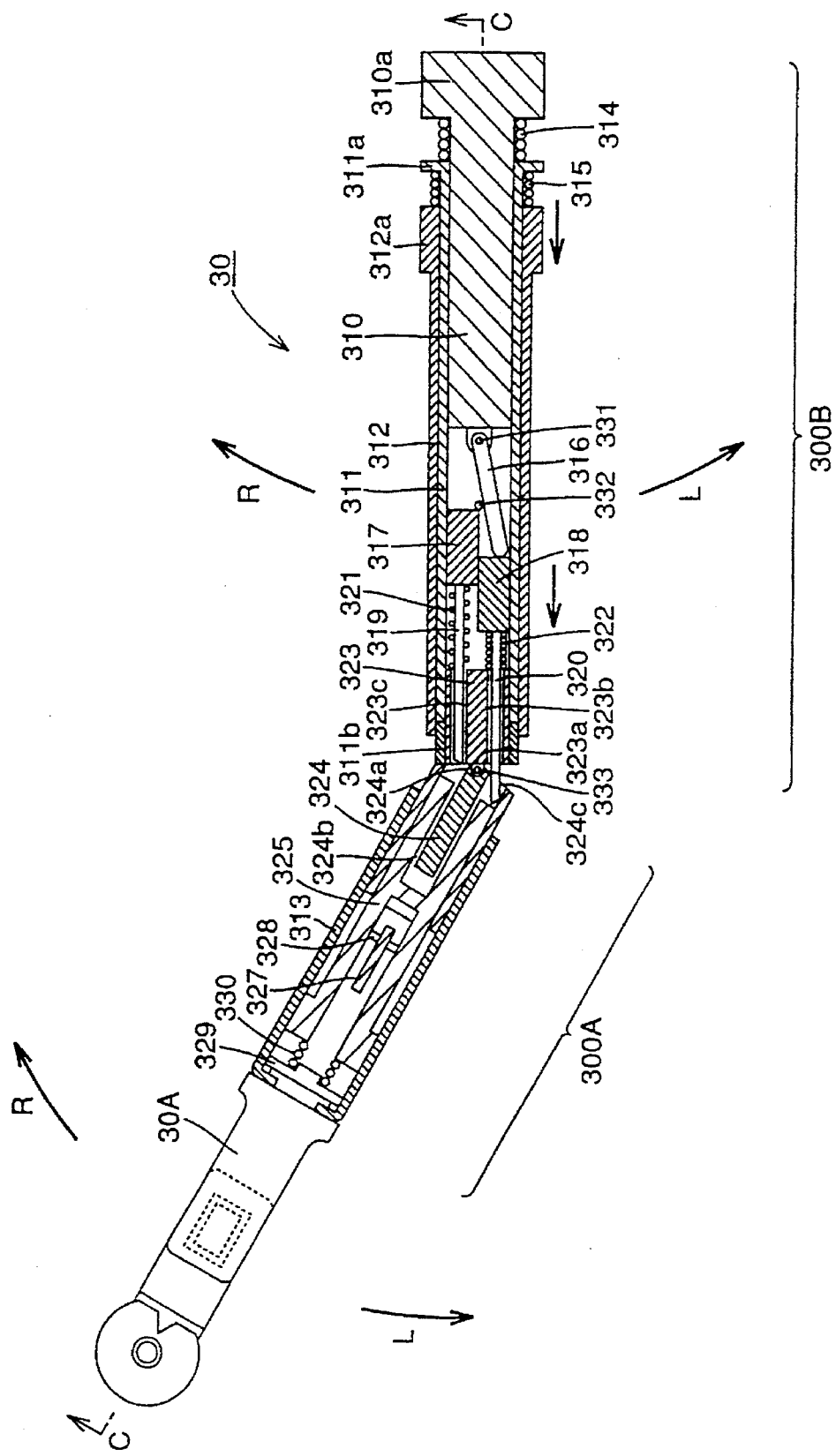
FIG. 13 is a second sectional view showing the operation of the ligative suturer according to the embodiment 2 of the present invention.
Figure 14:
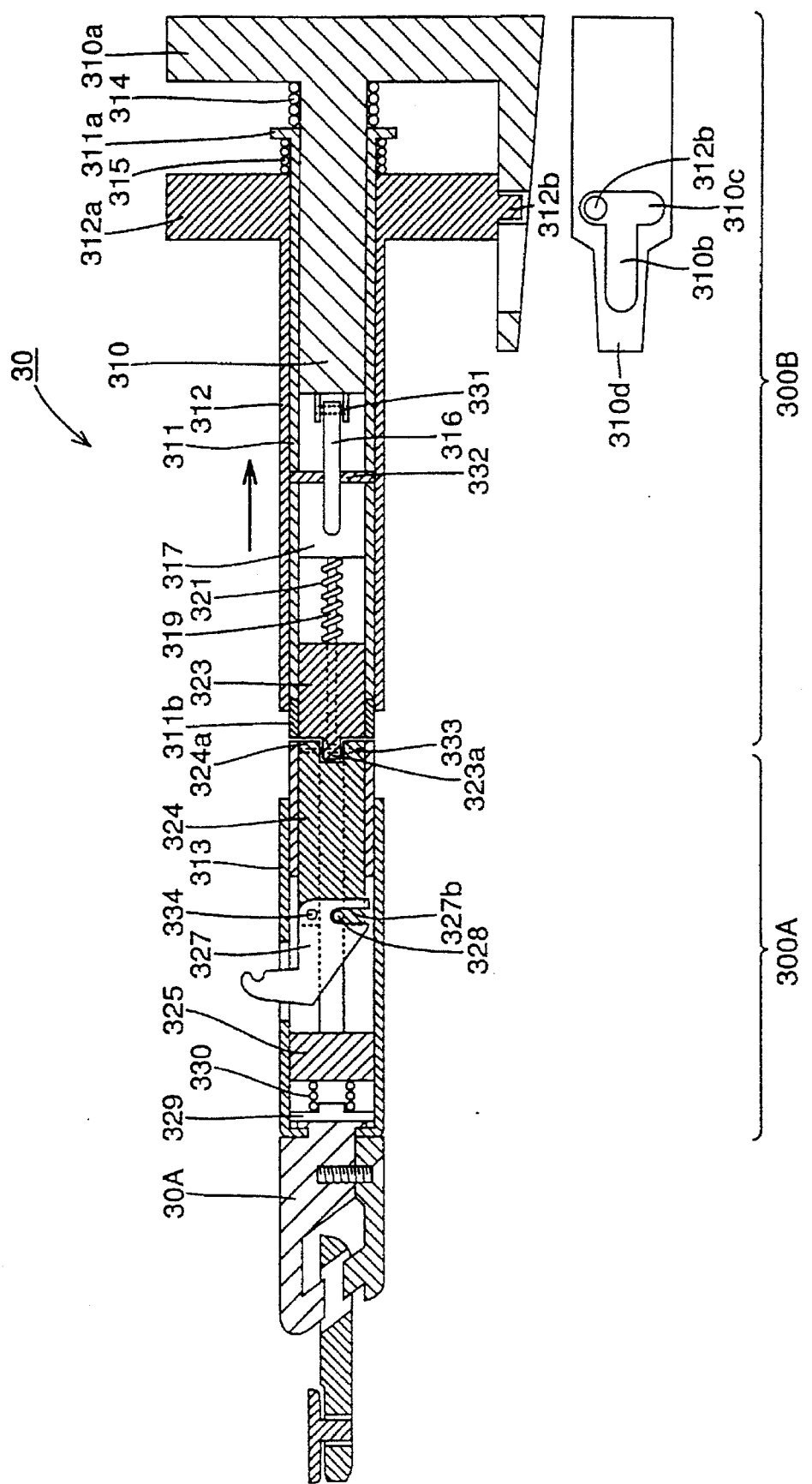
FIG. 14 is a sectional view taken along the line C—C in FIG. 13.

Referring to FIGS. 13 and 14, the first and second grips 312a and 310a are further grasped, whereby the second grip spring 314 is then compressed and the fourth rod member 310 is moved toward the forward end with respect to the third rod member 311.

Following this, the second slide member 318 is moved toward the forward end by the lever member 316, and the second contact bar 320 is further moved toward the forward end to come into contact with the working bar 325 and press the same against the forward end while moving the overall first rod 300A along arrow R.

As shown in the sectional view of FIG. 14, the rotation axis 334 of the thread guard member 327 is fixed to the first connection block 324 while the engaging pin 328 is moved toward the forward end with the working bar 325, whereby the thread guard member 327 is rotated clockwise so that a thread guard part 327a of the thread guard member 327 is outwardly exposed from the first rod 300A.

Further, the locking bar 312b which is provided on the first grip 312 is positioned on an end of the second groove 310c as shown in FIG. 14 for locking the first and second grips 312 and 310, whereby the ligative suturer 30 can be held in the state shown in FIGS. 13 and 14.

Figure 15:
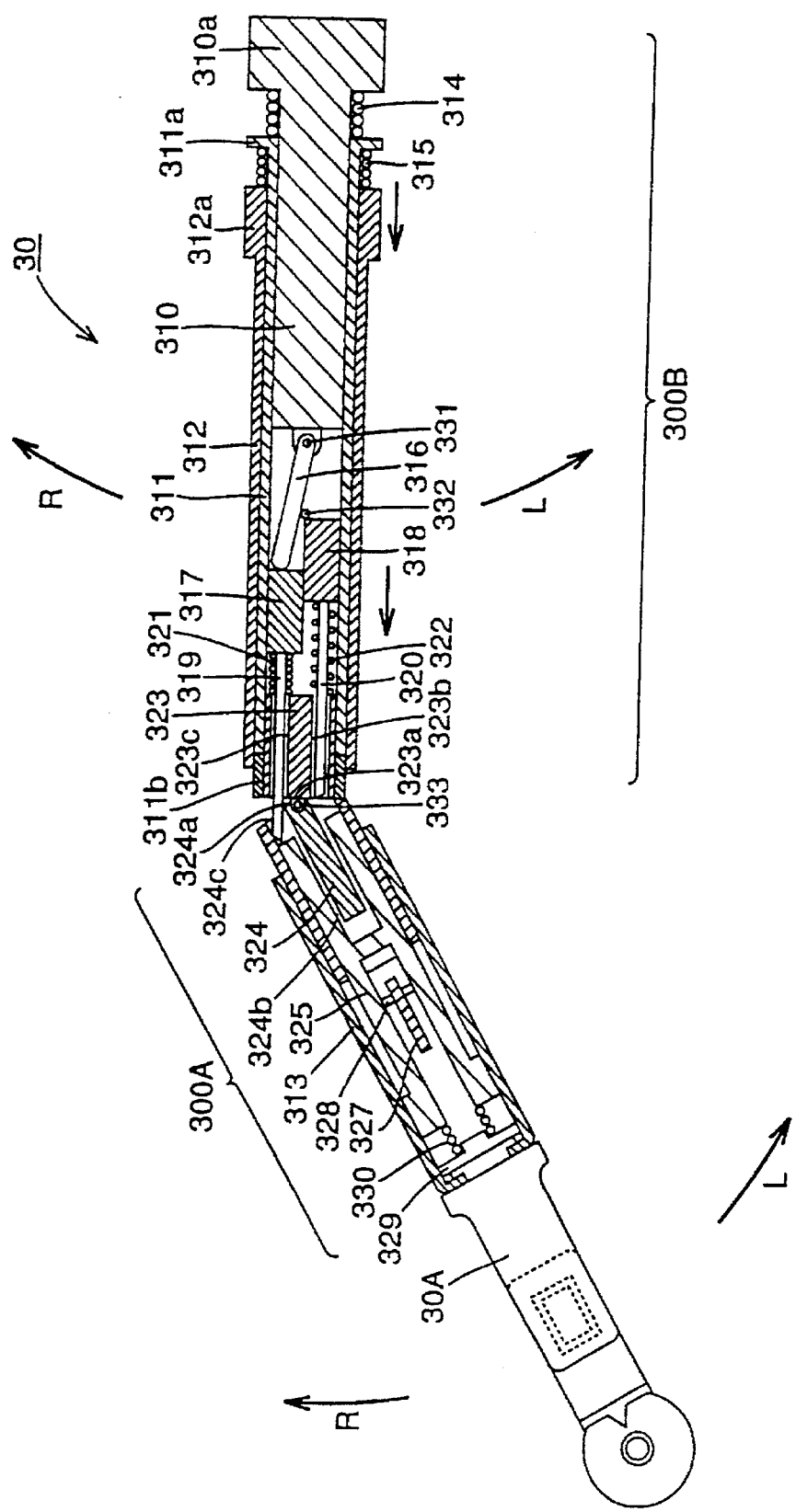
FIG. 15 is a sectional view showing another operating state of the ligative suturer according to the embodiment 2 of the present invention.

In the operation shown in FIGS. 11 to 14, the lever member 316 is inclined along arrow L thereby inclining the first rod 300A along arrow R. Also when the lever member 316 is inclined along arrow R, the first rod 300A can be bent along arrow L by a similar operation, as shown in FIG. 15.

Figure 16:
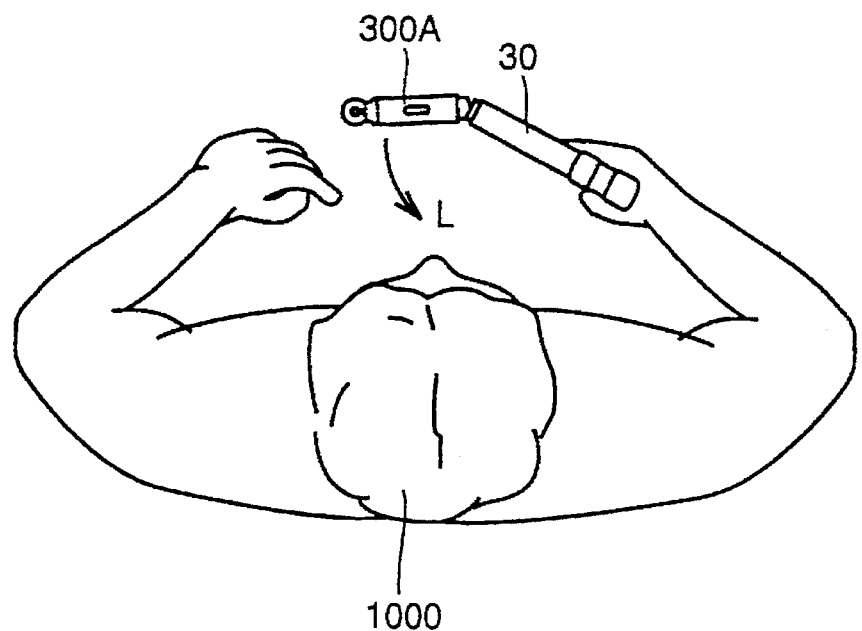
FIGS. 16 and 17 are first and second diagrams for illustrating the advantage of the ligative suturer according to the embodiment 2 of the present invention.

In the ligative suturer 30 having the aforementioned structure, therefore, the overall first rod 300A can be bent in a direction which is opposite to that of inclination of the lever member 316. Therefore, when an operator 1000 holds the ligative suturer 30 with his right hand as shown in FIG. 16, for example, the lever member 316 is inclined along arrow R in accordance with the gravity, whereby the first rod 300A is inclined along arrow L. In other words, the first rod 300A is bent toward the operator 1000, whereby operability of the ligative suturer 30 can be improved in an endoscopic surgical operation.

Figure 17:
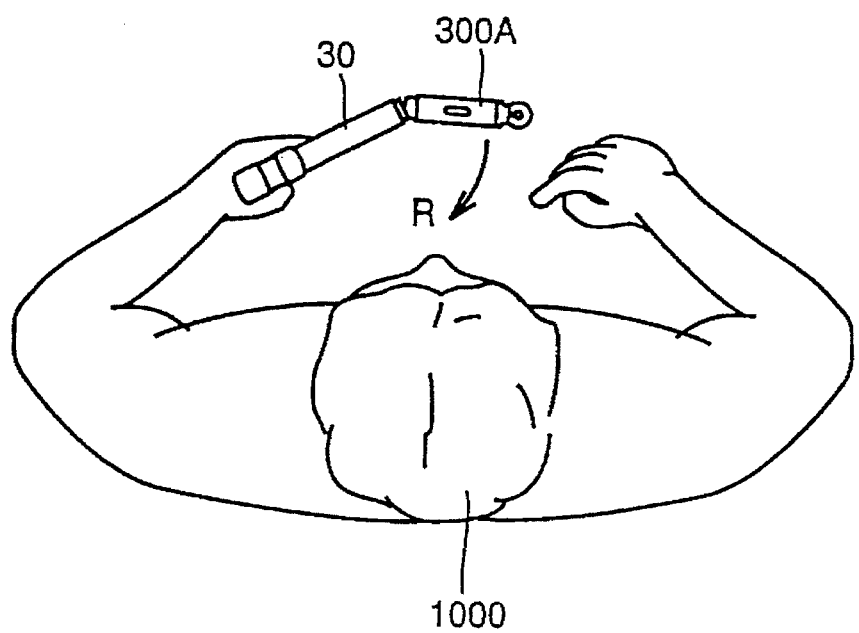

Also when the operator 1000 handles the ligative suturer 30 with his left hand as shown in FIG. 17, the lever member 316 is inclined along arrow L in accordance with the gravity, whereby the first rod 300A is bent along arrow R toward the operator 1000.

Description is now made on the procedure of an operation for suturing an opening 20 in an endoscopic surgical operation with the ligative suturer 30 having the aforementioned structure with reference to FIGS. 18 to 23.

Figure 18:
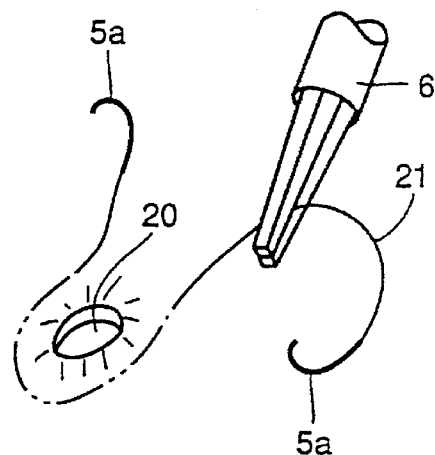
FIGS. 18 to 23 are first to sixth diagrams showing an operative procedure with the ligative suturer according to the embodiment 2 of the present invention.

Referring to FIG. 18, the operative thread 21 having operative needles 5a on both ends thereof is sewn around the opening 20 with the forceps 6.

Figure 19:
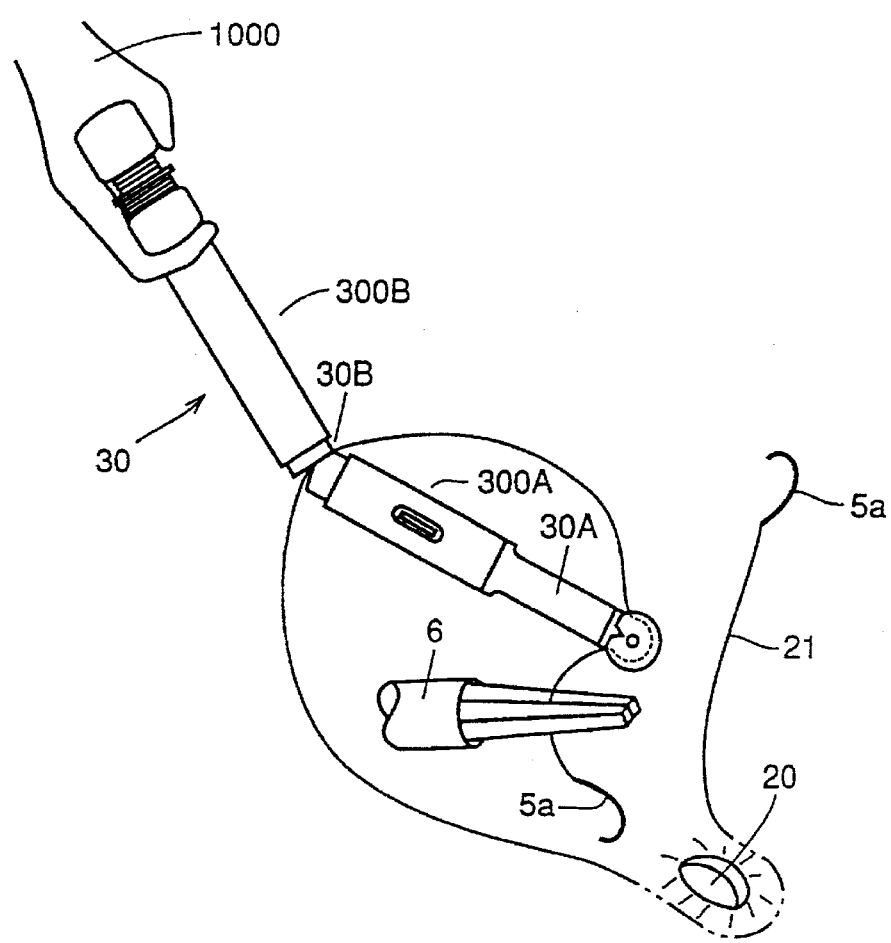
Figure 20:
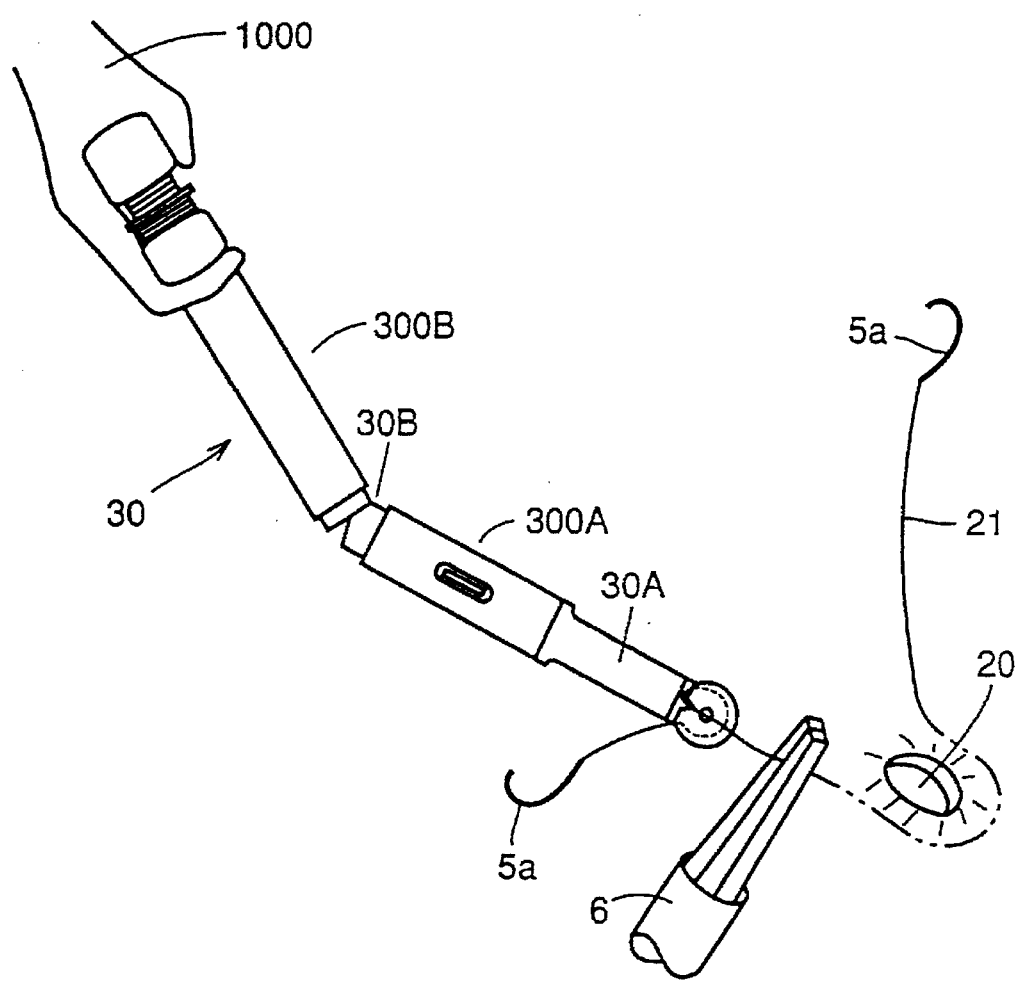
Figure 21:
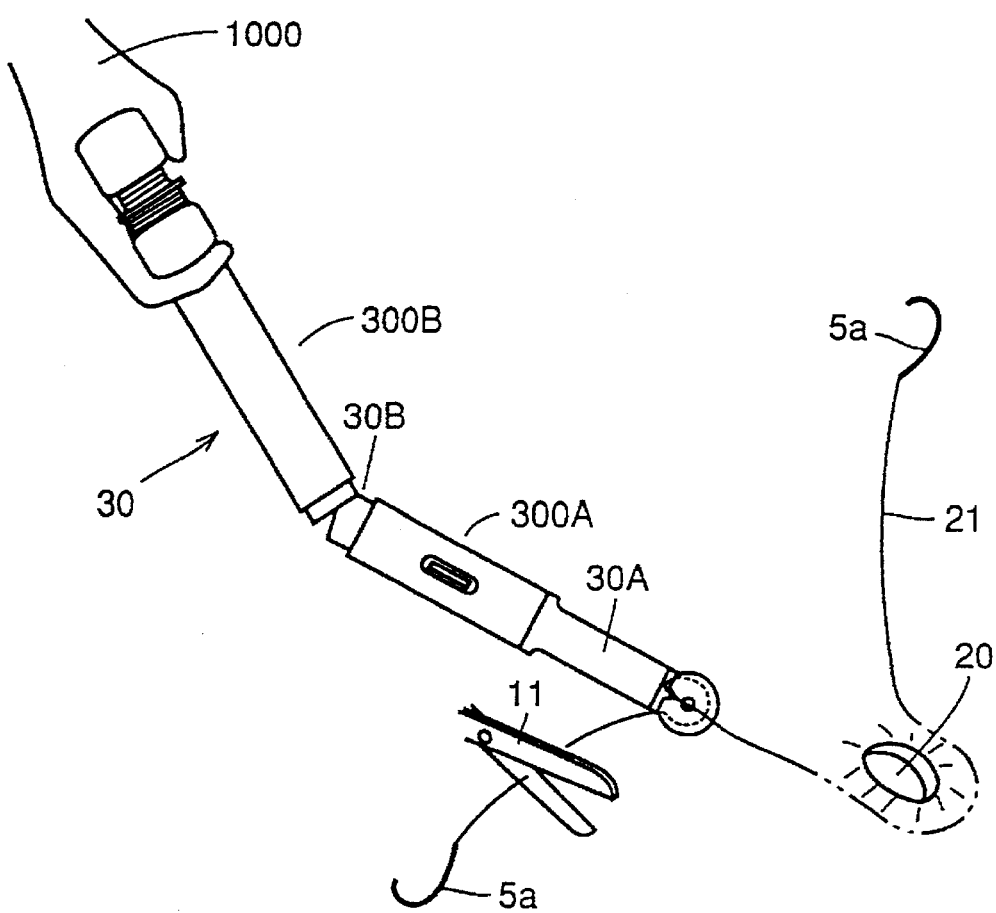

Referring to FIG. 19, the first end of the operative thread 21 is first held in the bent portion 30B between the first and second rods 300A and 300B of the ligative suturer 30, and made to go half around the thread support part 304 of the ligative sutural member 30A as such. Thereafter the second end of the operative thread 21 is made to engage with the notched portion 305, as shown in FIG. 20. Thereafter the operative needle 5a provided on the first end of the operative thread 21 is removed with scissors 11, as shown in FIG. 21.

Figure 22:
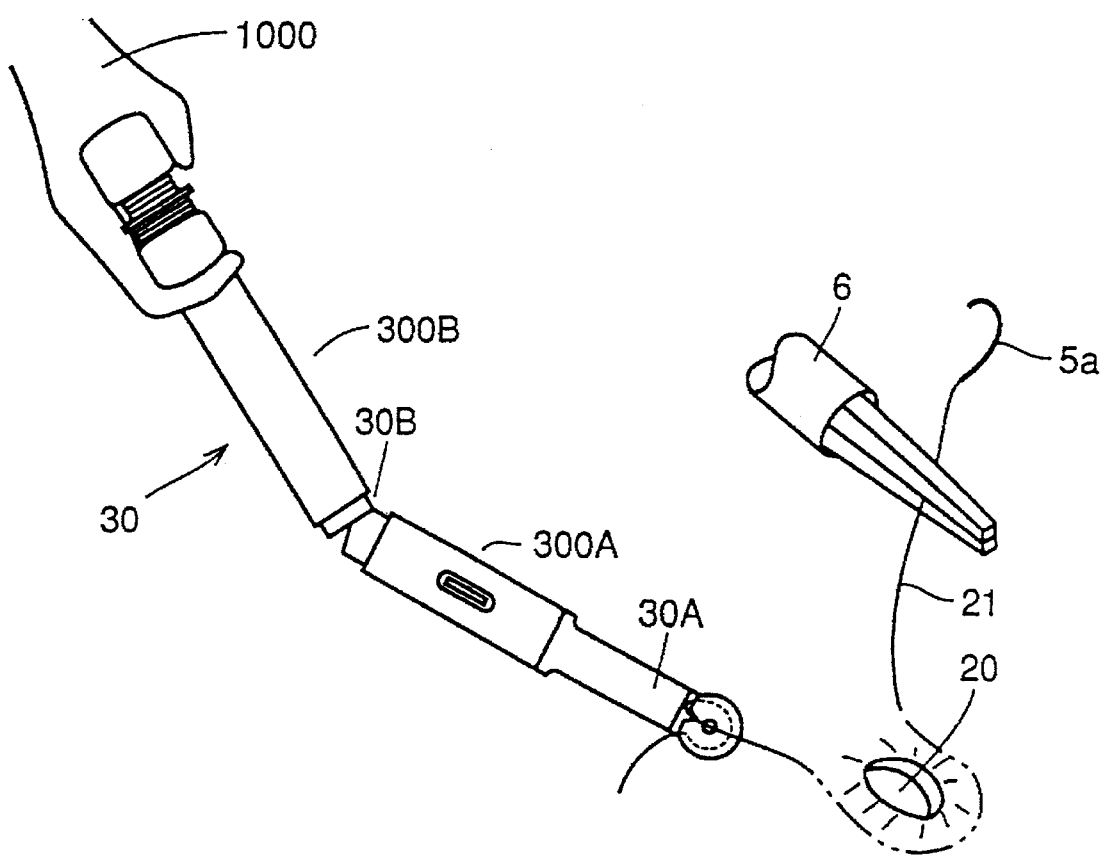
Figure 23:
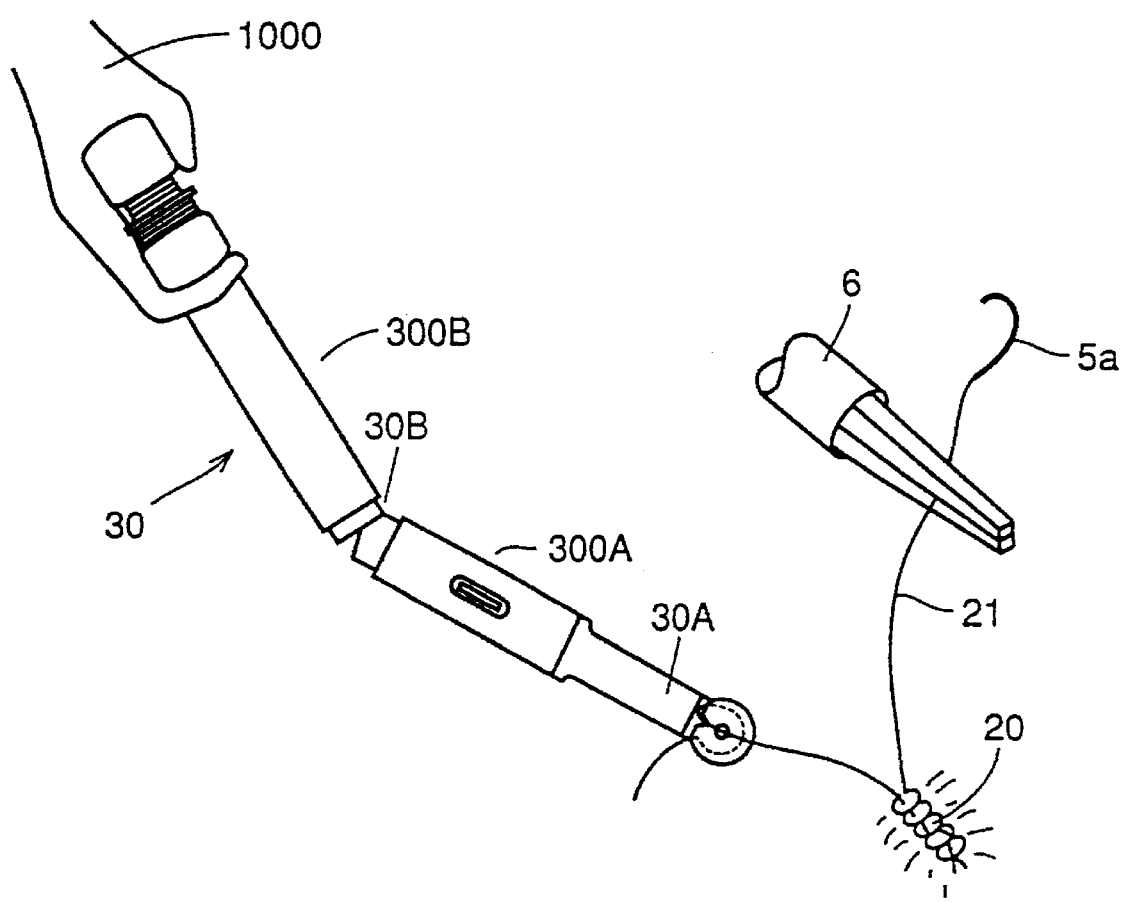
Figure 37:
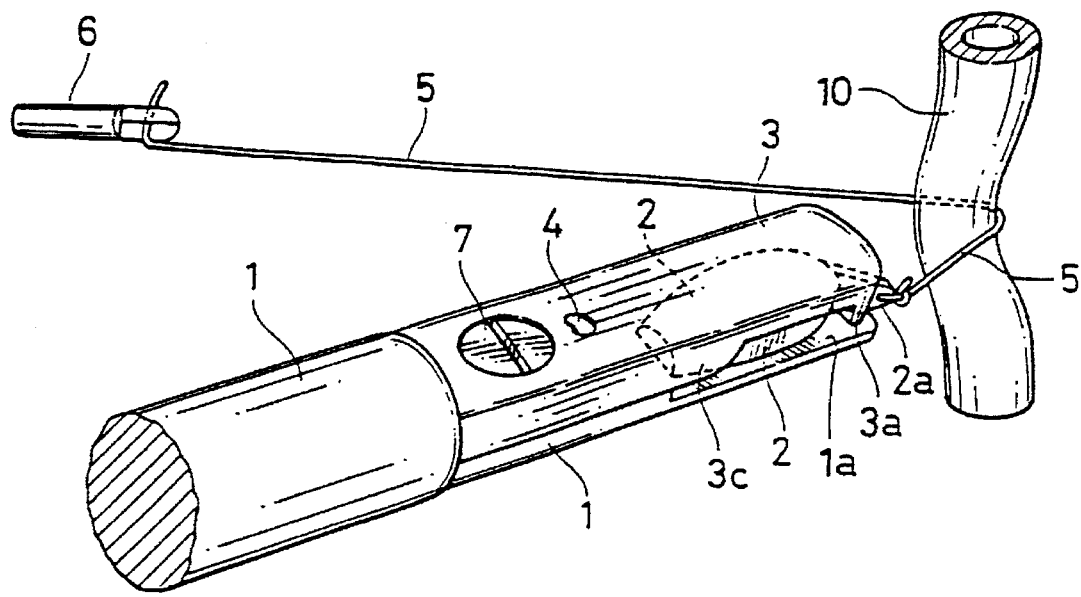
FIGS. 37 to 58 are first to twenty-second diagrams for illustrating a ligative operation with the ligation apparatus shown in FIG. 33.
Figure 38:
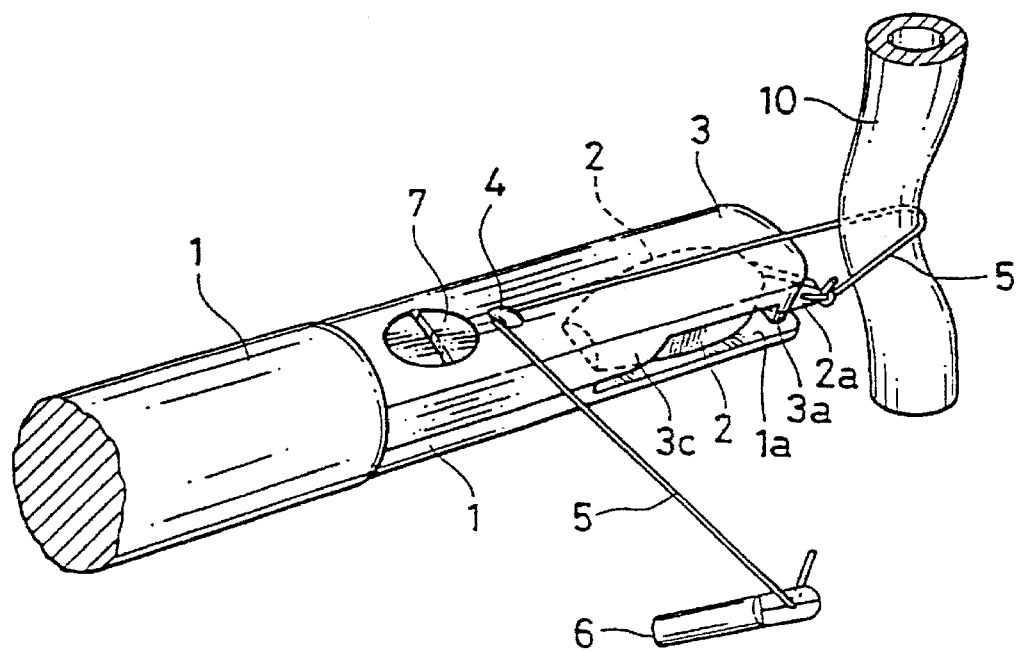
Figure 39:
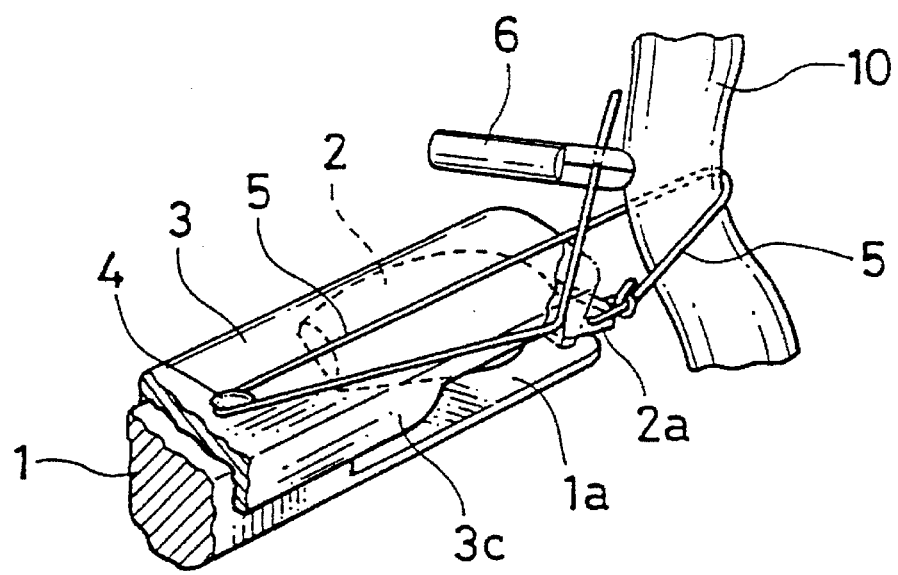
Figure 40:
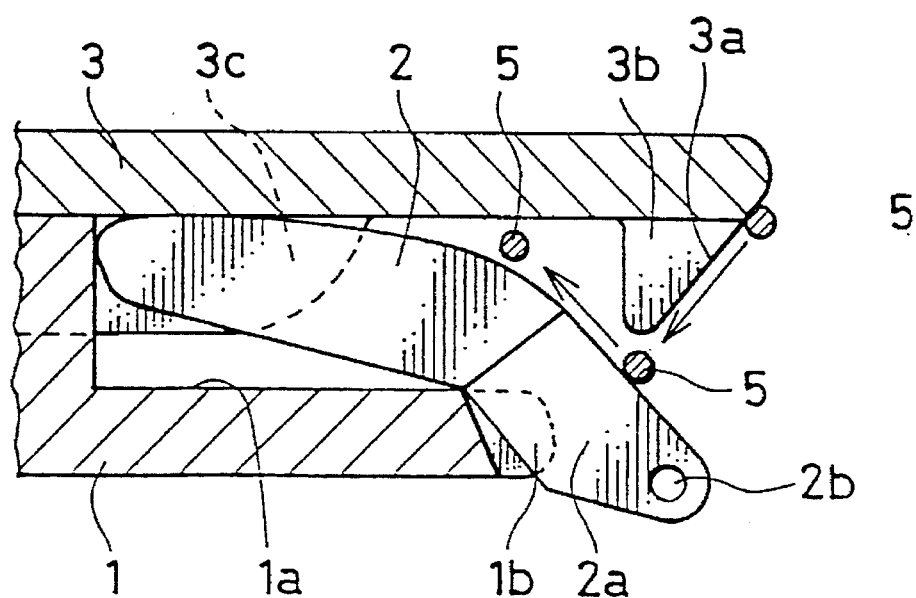
Figure 41:
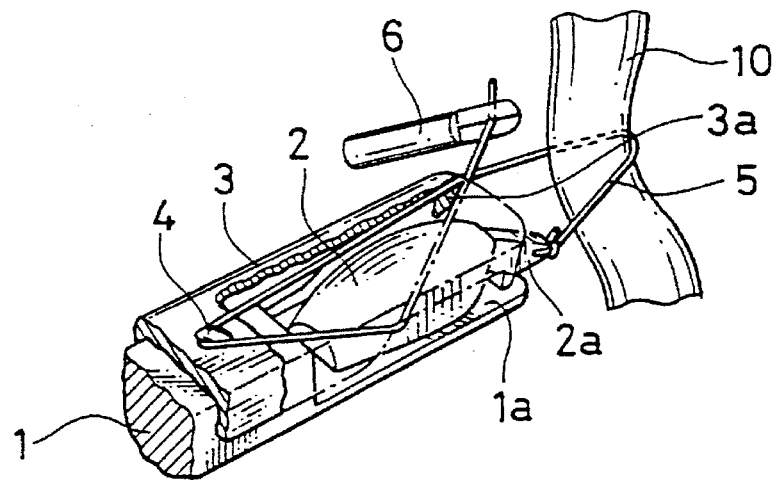
Figure 42:
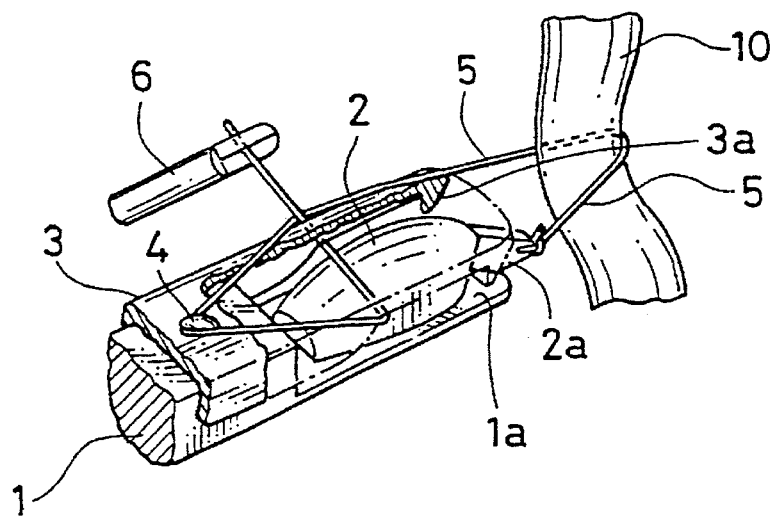
Figure 43:
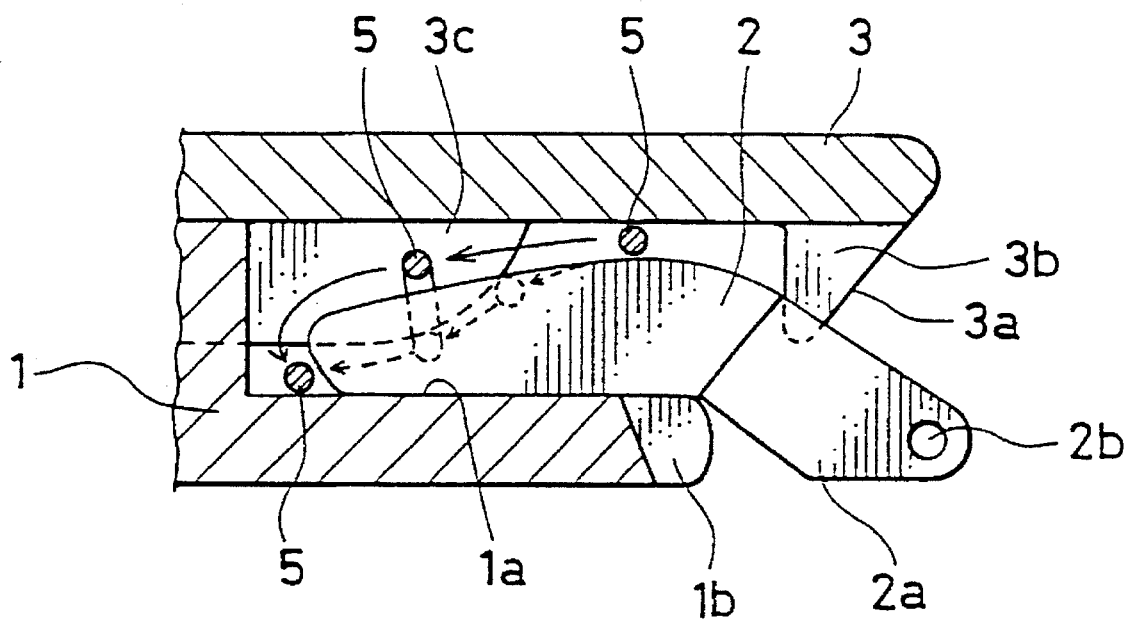
Figure 44:
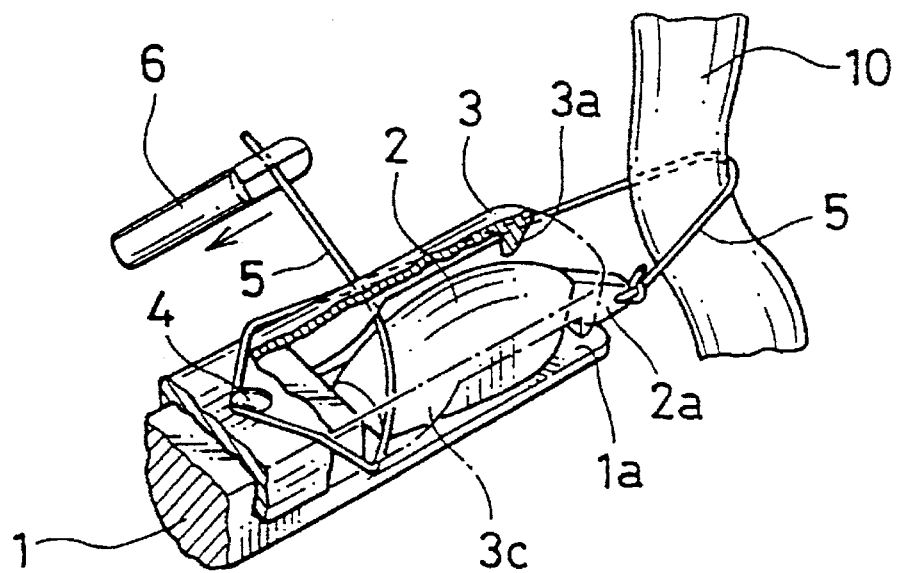
Figure 45:
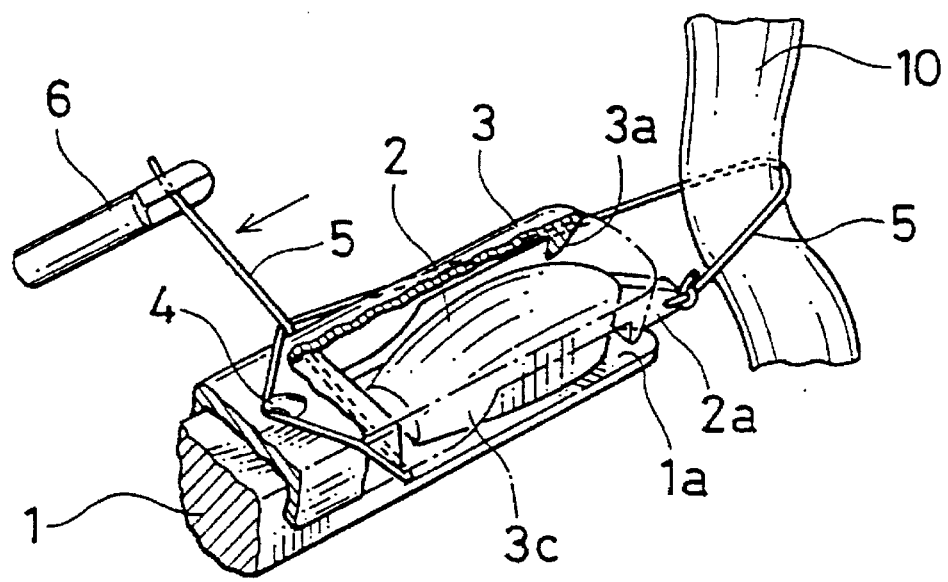
Figure 46:
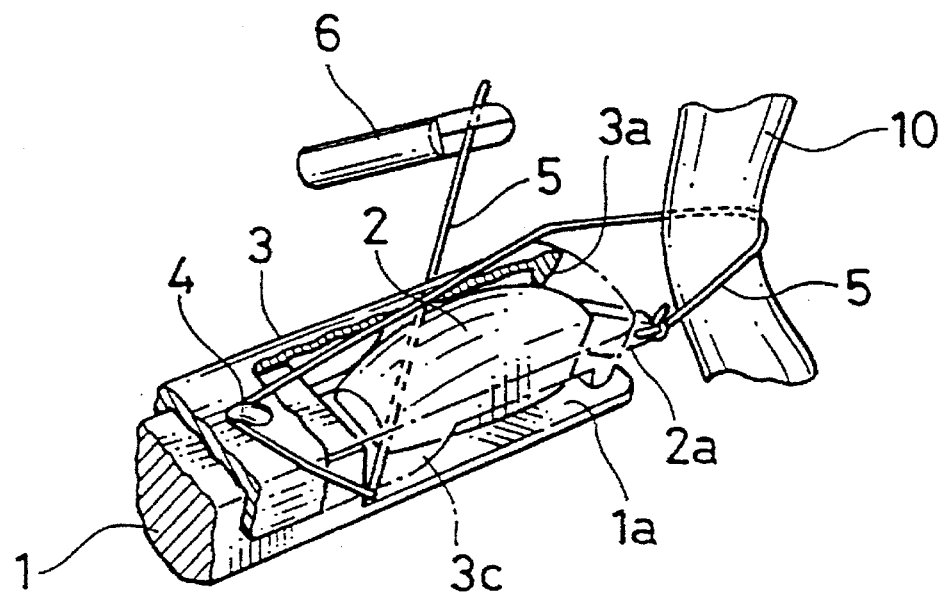
Figure 47:
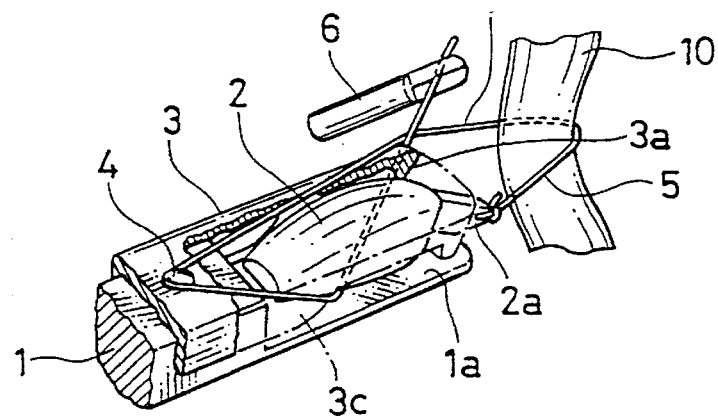
Figure 48:
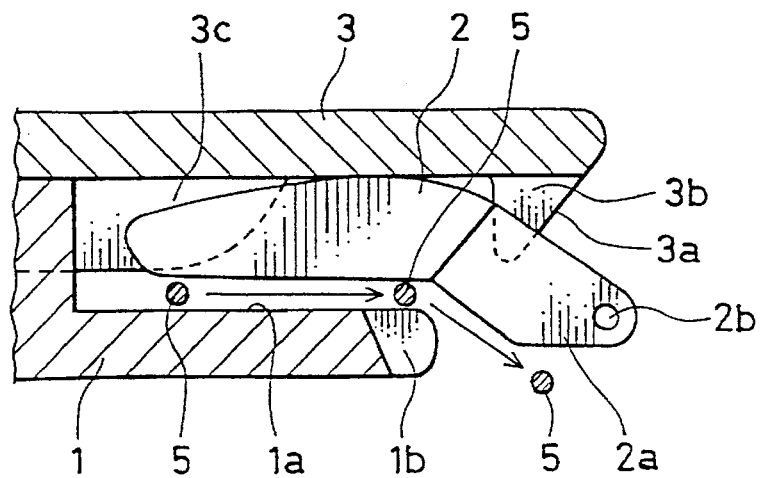
Figure 49:
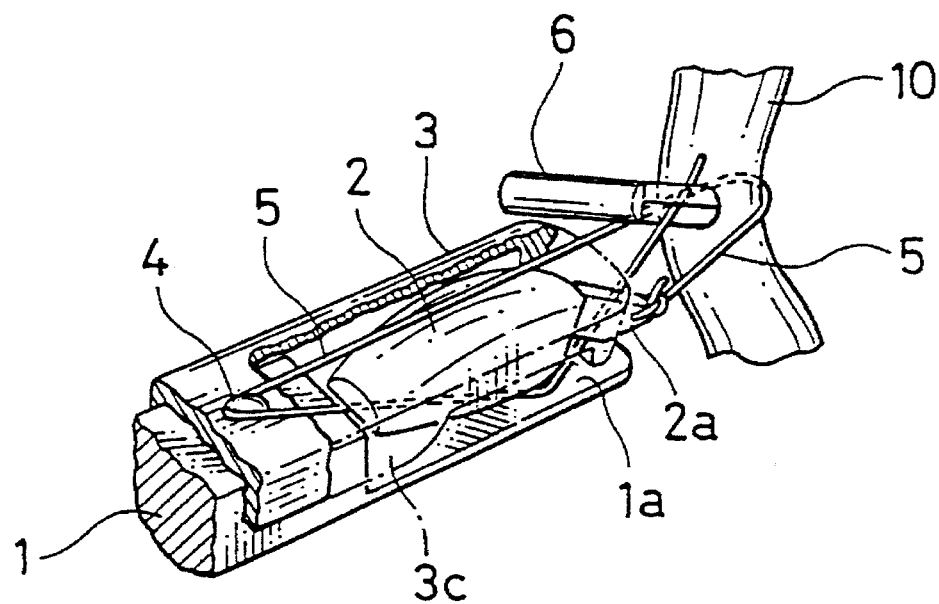
Figure 50:
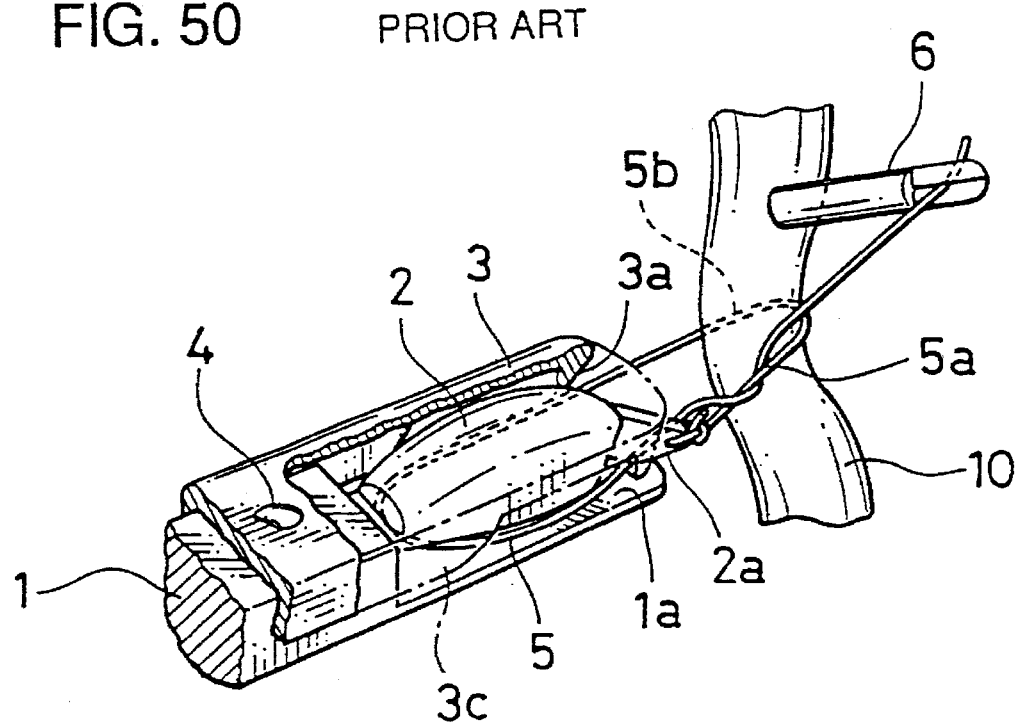
Figure 51:
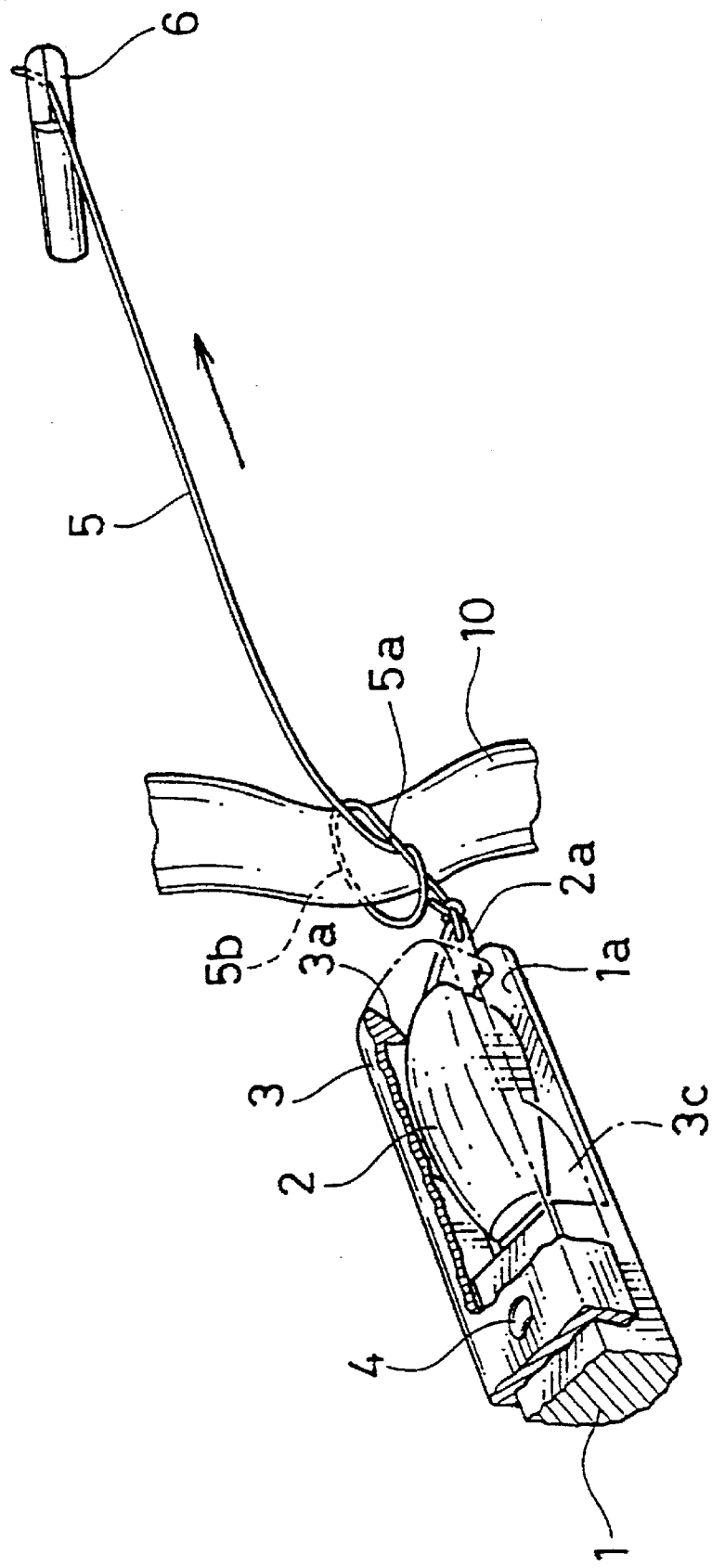
Figure 52:
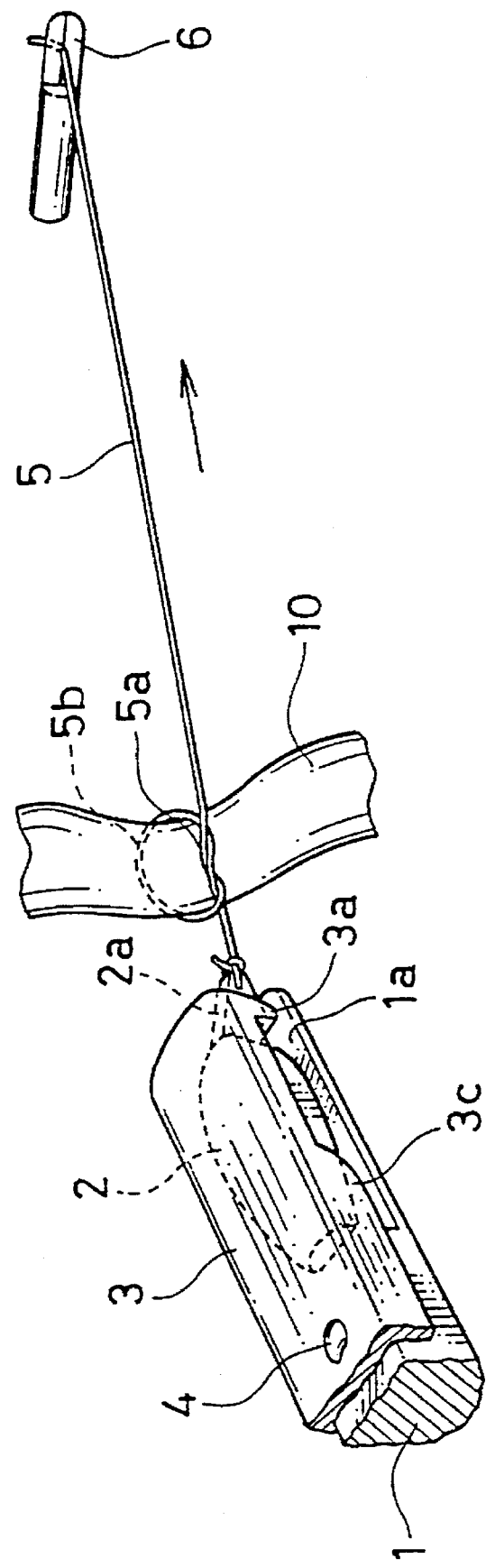
Figure 53:
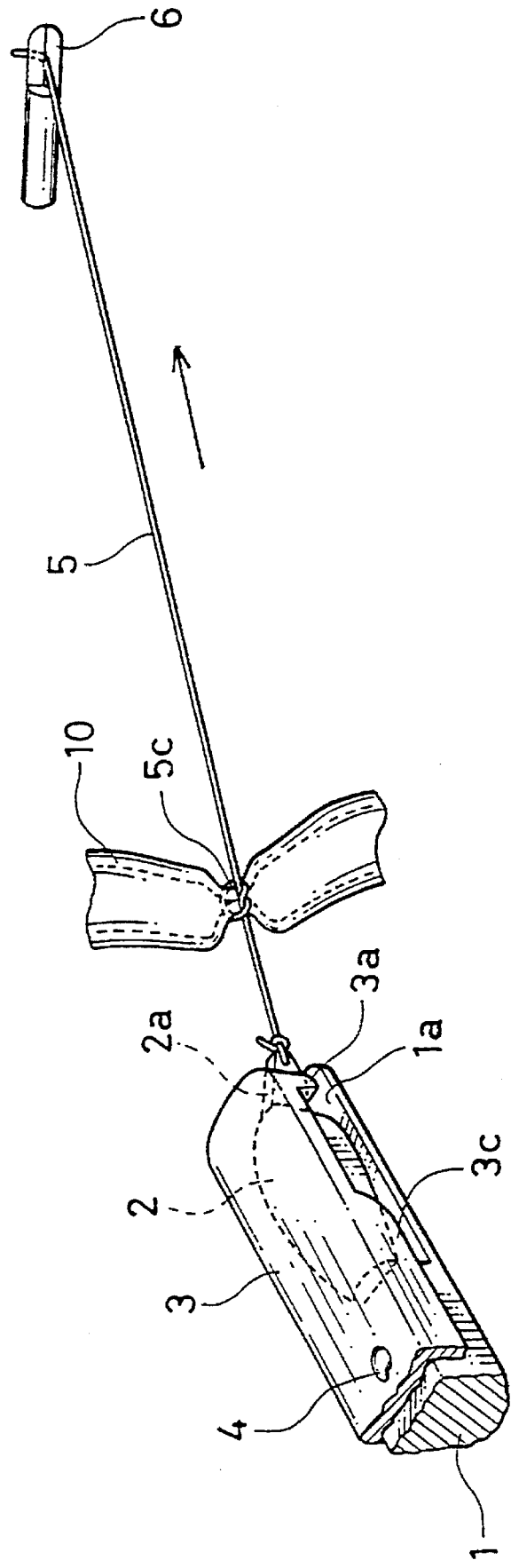
Figure 54:
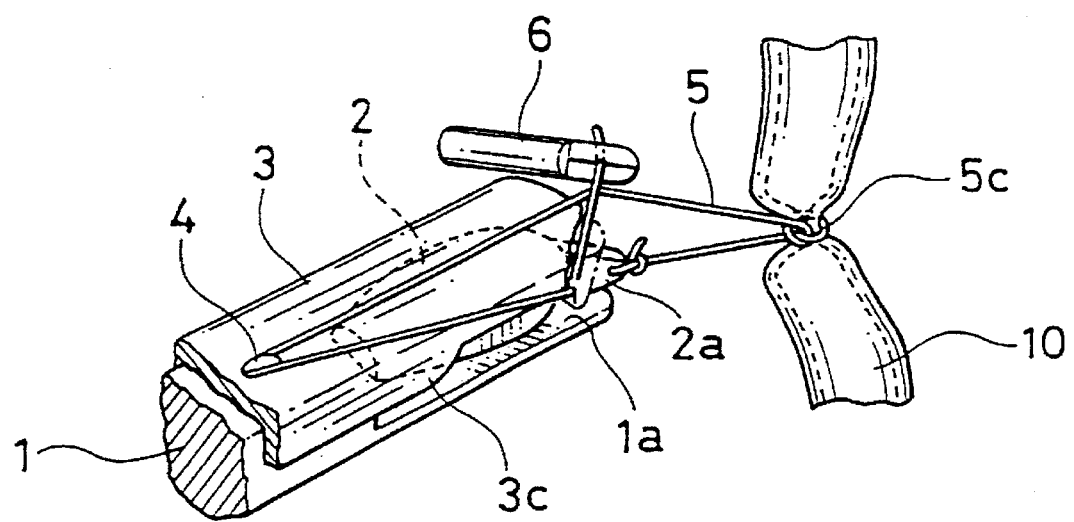
Figure 55:
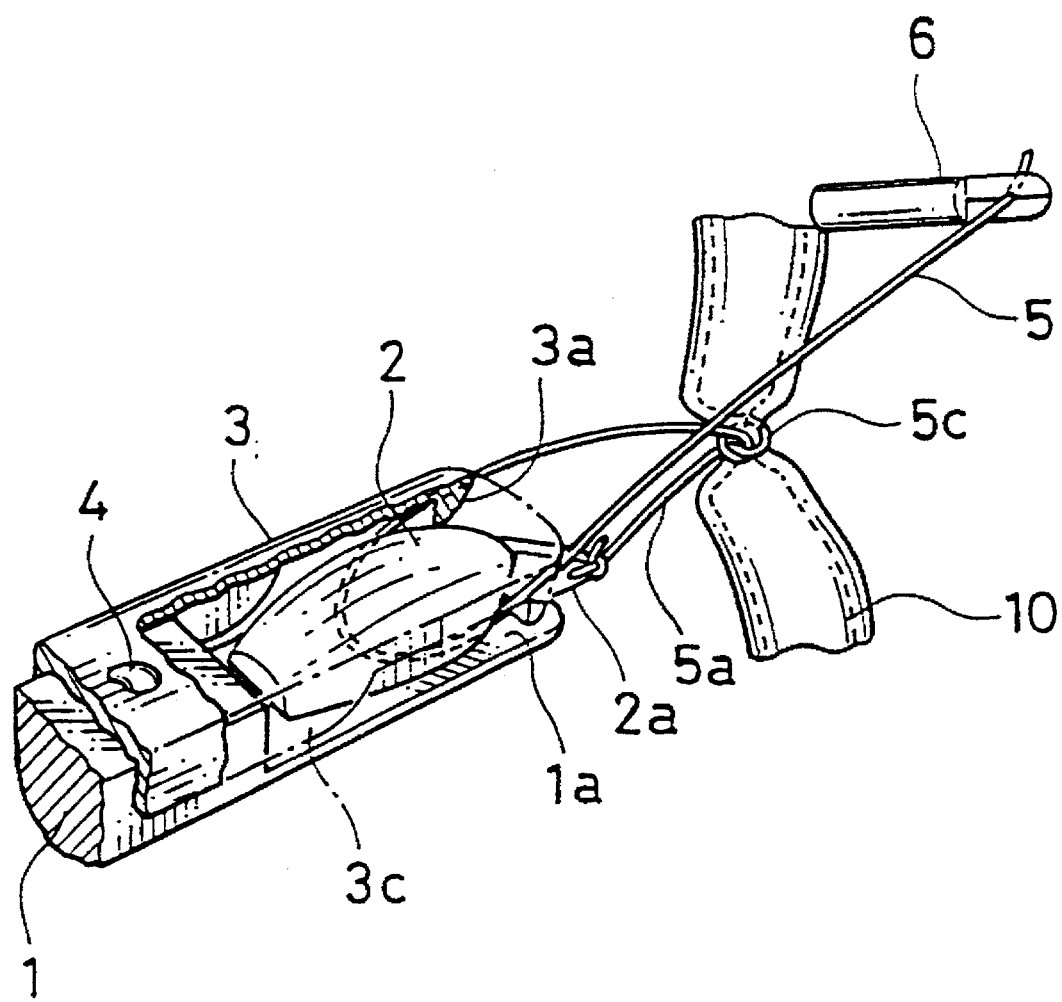
Figure 56:
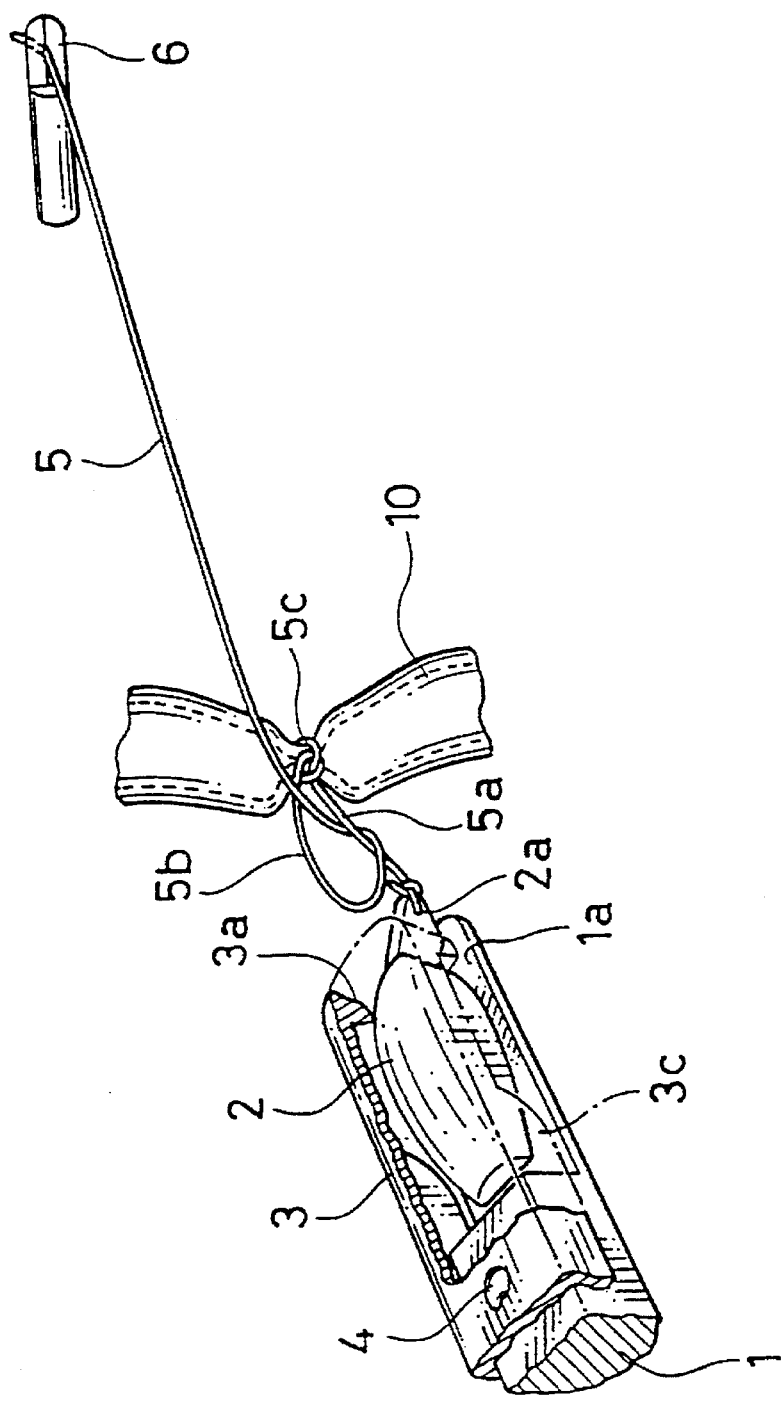
Figure 57:
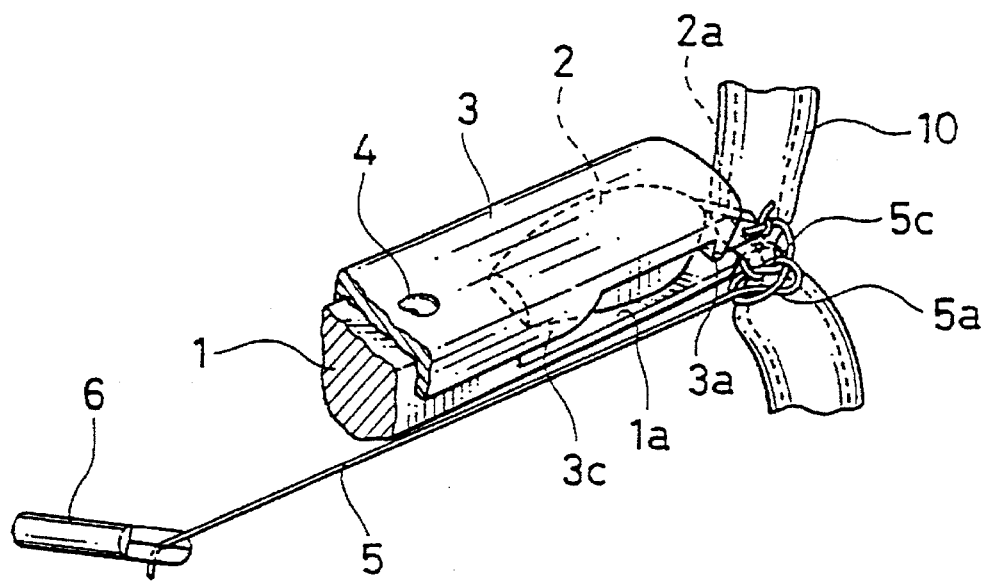
Figure 58:
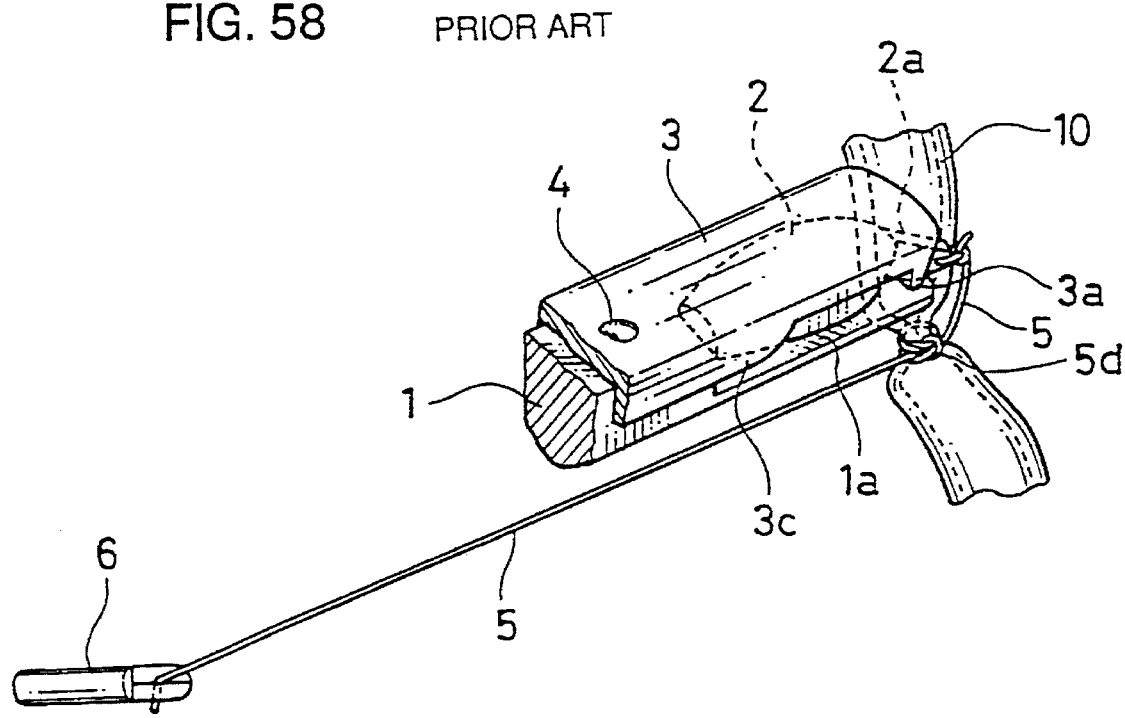
Figure 59:
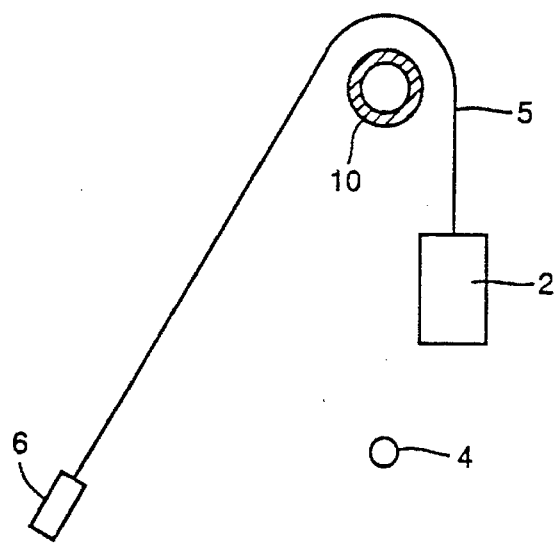
FIGS. 59 to 66 are first to eighth model diagrams for illustrating the ligative operation with the ligation apparatus shown in FIG. 33.
Figure 60:
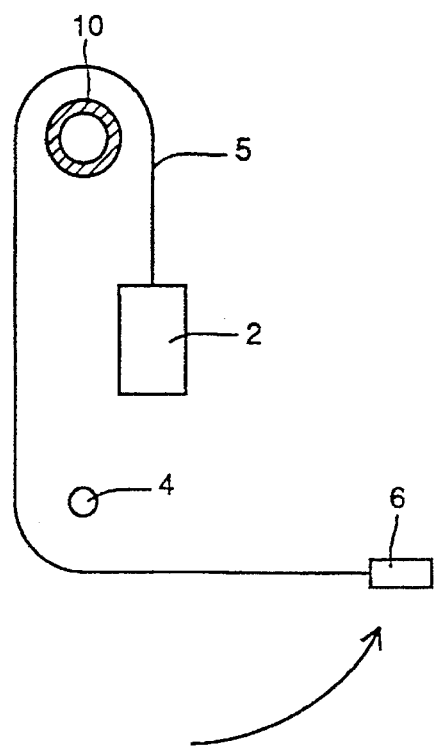
Figure 61:
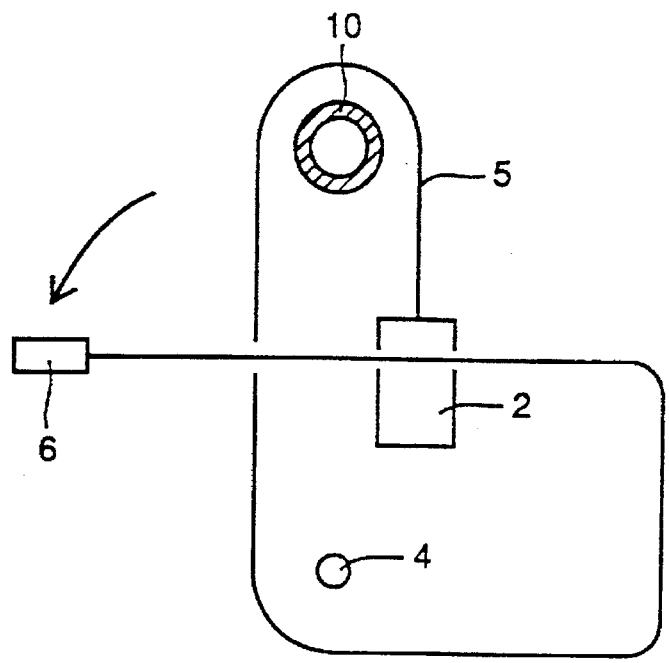
Figure 62:
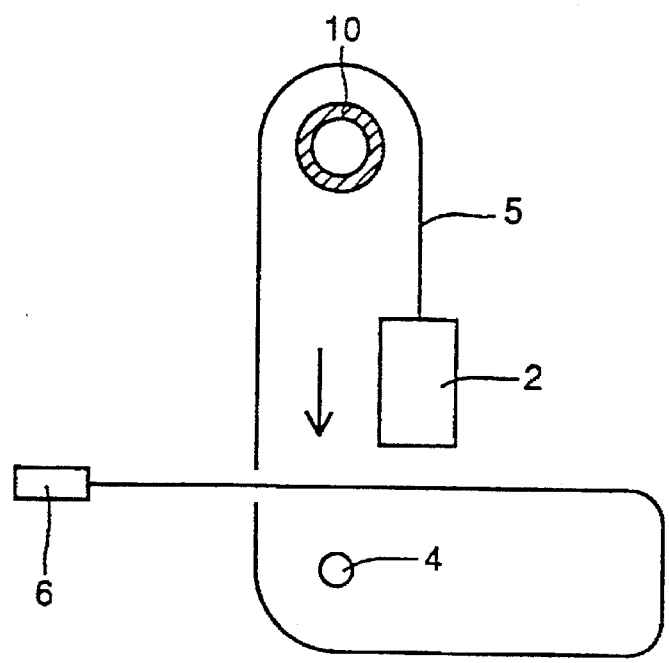
Figure 63:
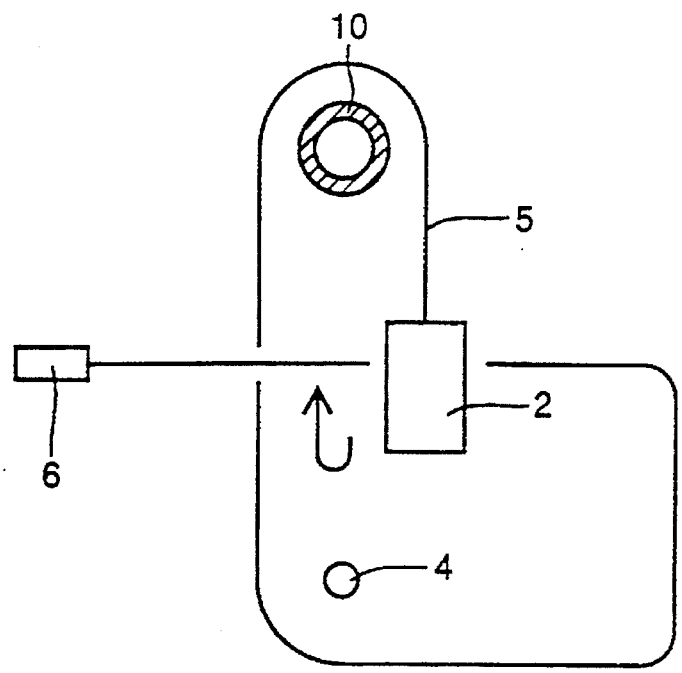
Figure 64:
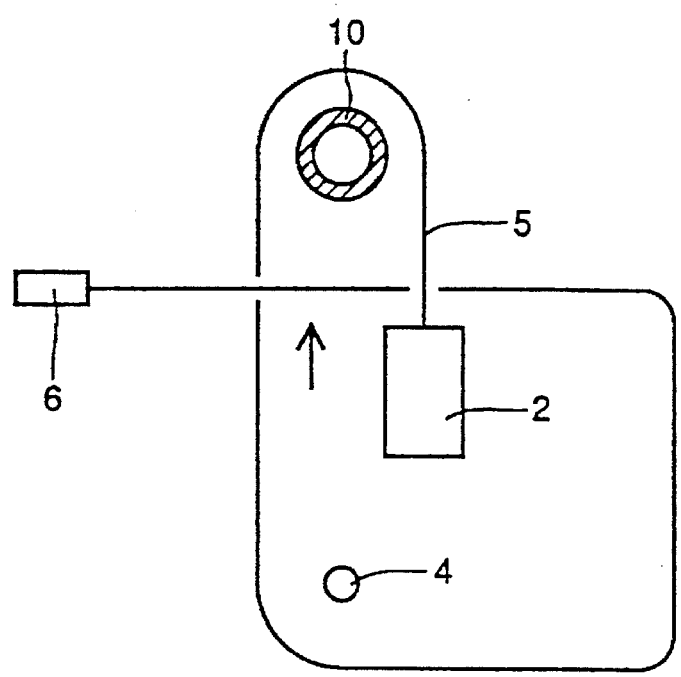
Figure 65:
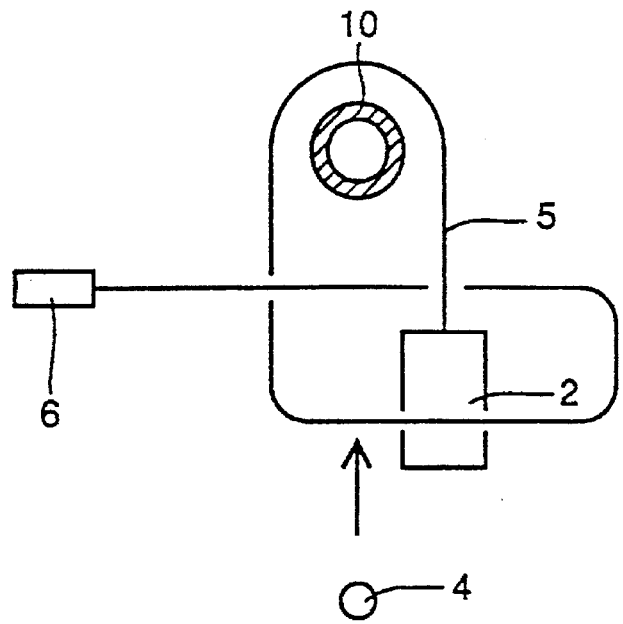
Figure 66:
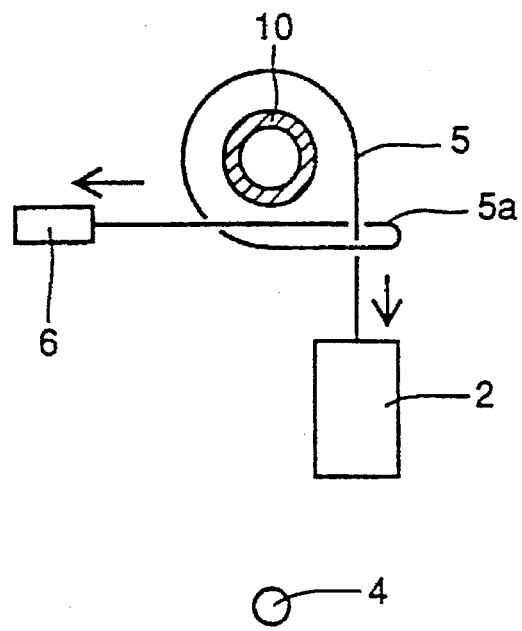

Then, the operative thread 21 is released from the bent portion 30B as shown in FIG. 22, whereby the first end of the operative thread 21 engages with the ligative sutural member 30A of the ligative suturer 30 so that the second end can be handled with the forceps 6, similarly to the state shown in FIG. 37 with reference to the prior art. Thereafter a sutural operation which is similar to that shown in FIGS. 37 to 66 with reference to the prior art is carried out, thereby suturing the opening 20 as shown in FIG. 23.

At this time, it is necessary to form not single but 5 to 6 knots in general. According to the ligative suturer 30, therefore, the sutural operation can be carried out while locking the first and second grips 312 and 310, thereby remarkably reducing the burden on the operator.

The thread support part 304 has a substantially circular shape and the notched portion 305 is provided on the rear end thereof, whereby the operative thread 21 can be readily fixed by the notched portion 305 while being wound on the thread support part 304. Further, the operative thread 21 is centrally derived with respect to the ligative sutural member 30A, whereby the ligative sutural operation can be facilitated.

Figure 24:
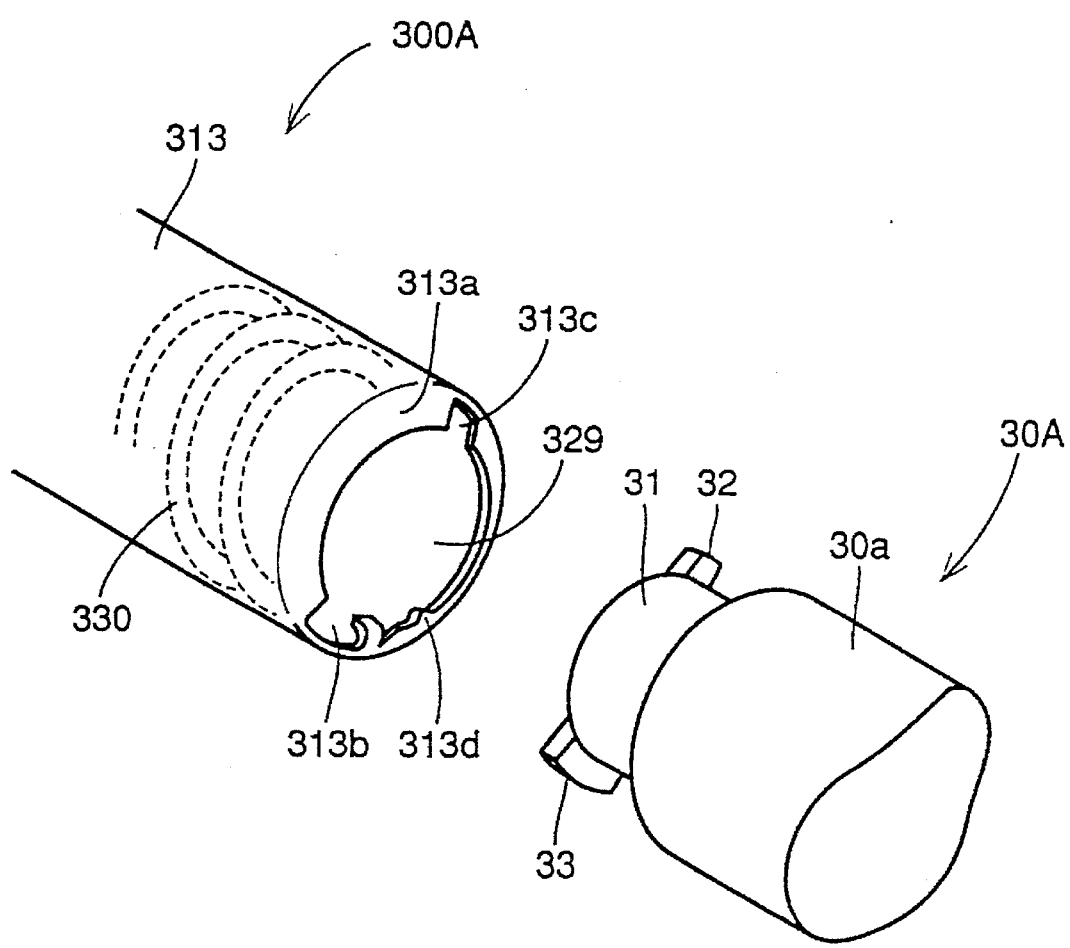
FIG. 24 is a perspective view showing an attachable/detachable structure of the ligative sutural member according to the present invention.

While the ligative sutural member 30A which is mounted on the forward end of the first rod 300A may be fixed thereto, it is preferable to attain such a state that only the ligative sutural member 30A is attachable to/detachable from the first rod 300A, in order to cope with thicknesses of operative threads which are varied with the types of operations. Such a structure of the ligative sutural member 30A which is attachable to/detachable from the first rod 300A is now described with reference to FIG. 24.

The body part 30a of the ligative sutural member 30A is provided on its rear end with a neck portion 31 which is smaller in diameter than the body part 30a. This neck portion 31 is provided on its outer peripheral surface with first and second convex parts 32 and 33 having different widths, to be opposed to each other toward the exterior.

On the other hand, the first rod member 313 of the first rod 300A is provided on its forward end with a flange part 313a having first and second window parts 313c and 313b in positions corresponding to the first and second convex parts 32 and 33 respectively, and an opening 329 for receiving the neck portion 31. The first rod member 313 is further provided on its forward end with a contact plate 329, which is adapted to block the opening 329, and a spring member 330 for urging the contact plate 329 toward the forward end.

When the neck portion 31 is inserted in the first rod member 313 so that the first and second convex parts 32 and 33 of the ligative sutural member 30A having the aforementioned structure are aligned with the window parts 313c and 313b and rotated clockwise until the first convex part 32 goes beyond an engaging convex part 313d which is provided on the flange part 313a, therefore, the ligative sutural member 30A can be reliably fixed to the first rod 300A, while the former can also be reliably detached from the latter.

While the ligative sutural member 30A of the aforementioned ligative suturer 30 is divided into the first and second body parts 30a and 30c as shown in FIG. 10, the present invention is not restricted to this structure but a ligative suturer 40A may have a body part of an integral structure, for example.

Figure 25:
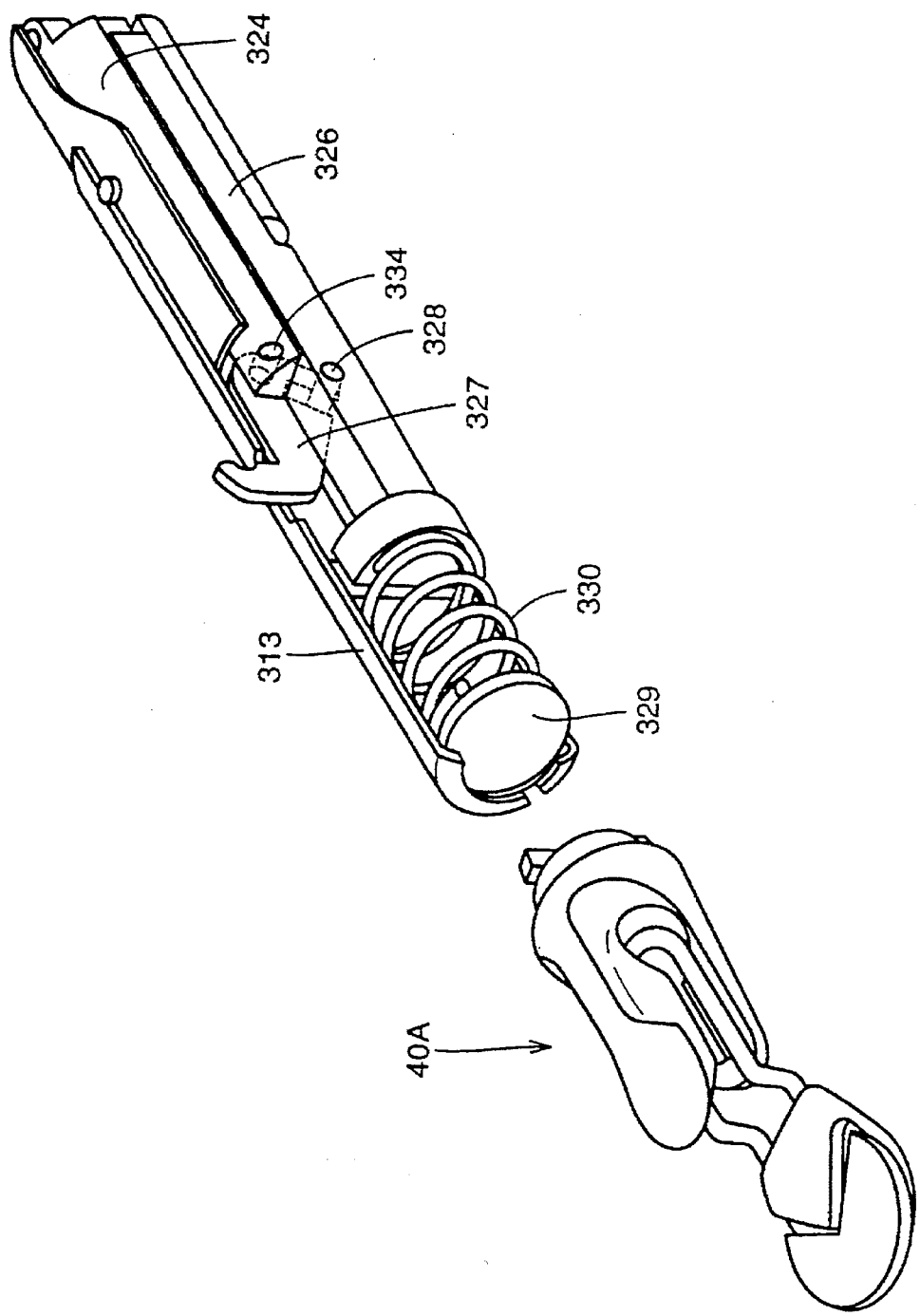
FIG. 25 is a general perspective view showing another structure of the ligative sutural member according to the present invention.
Figure 26:
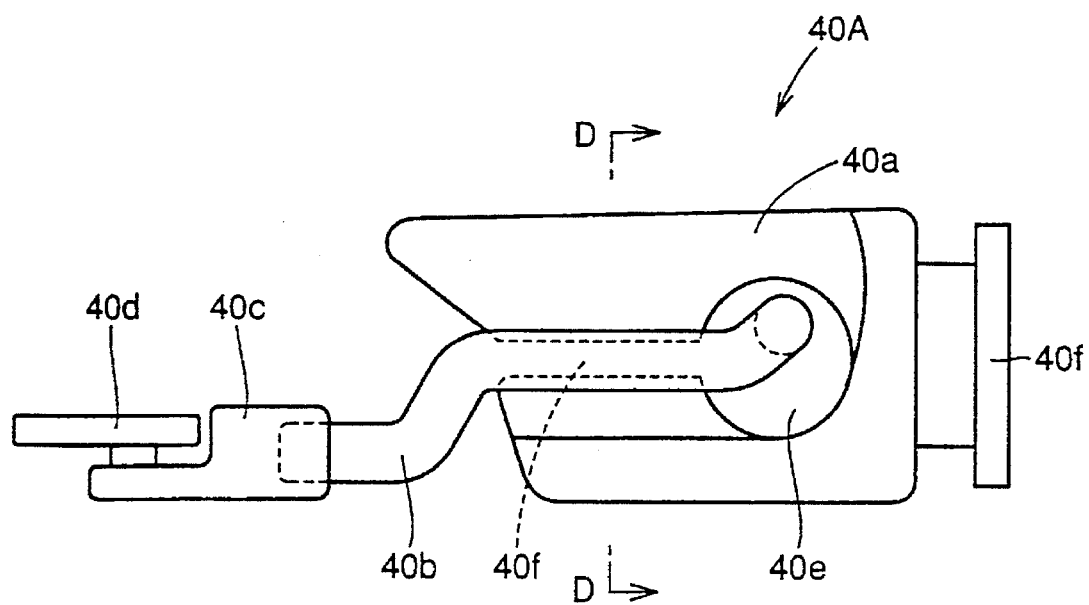
FIG. 26 is a side elevational view of the ligative sutural member shown in FIG. 25.
Figure 27:
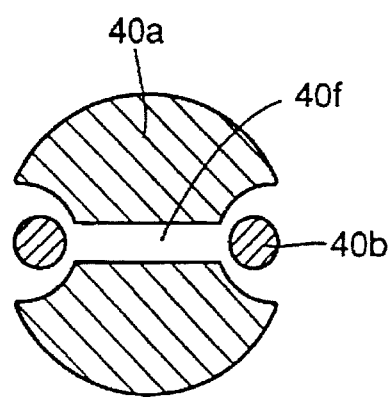
FIG. 27 is a sectional view taken along the line D—D in FIG. 26.

As shown in FIGS. 25 to 27, this ligative sutural member 40A has a body part 40a, an opening 40e which is formed to pass through the rear central portion of the body part 40a, and a slit 40f, communicating with the opening 40e, which is formed toward the forward end, for example. Further, a clip 40b is provided to be downwardly bent toward the forward end for passing through the opening 40e and holding the slit 40f from both sides, and a thread guard base 40c and a thread support part 40d are mounted on the forward end of the clip 40b. The thread guard base 40c has a convex part extending toward the forward end and the thread support part 40d engaging with a concave part and having a notch along the concave part, as shown in FIG. 28.

Figure 28:
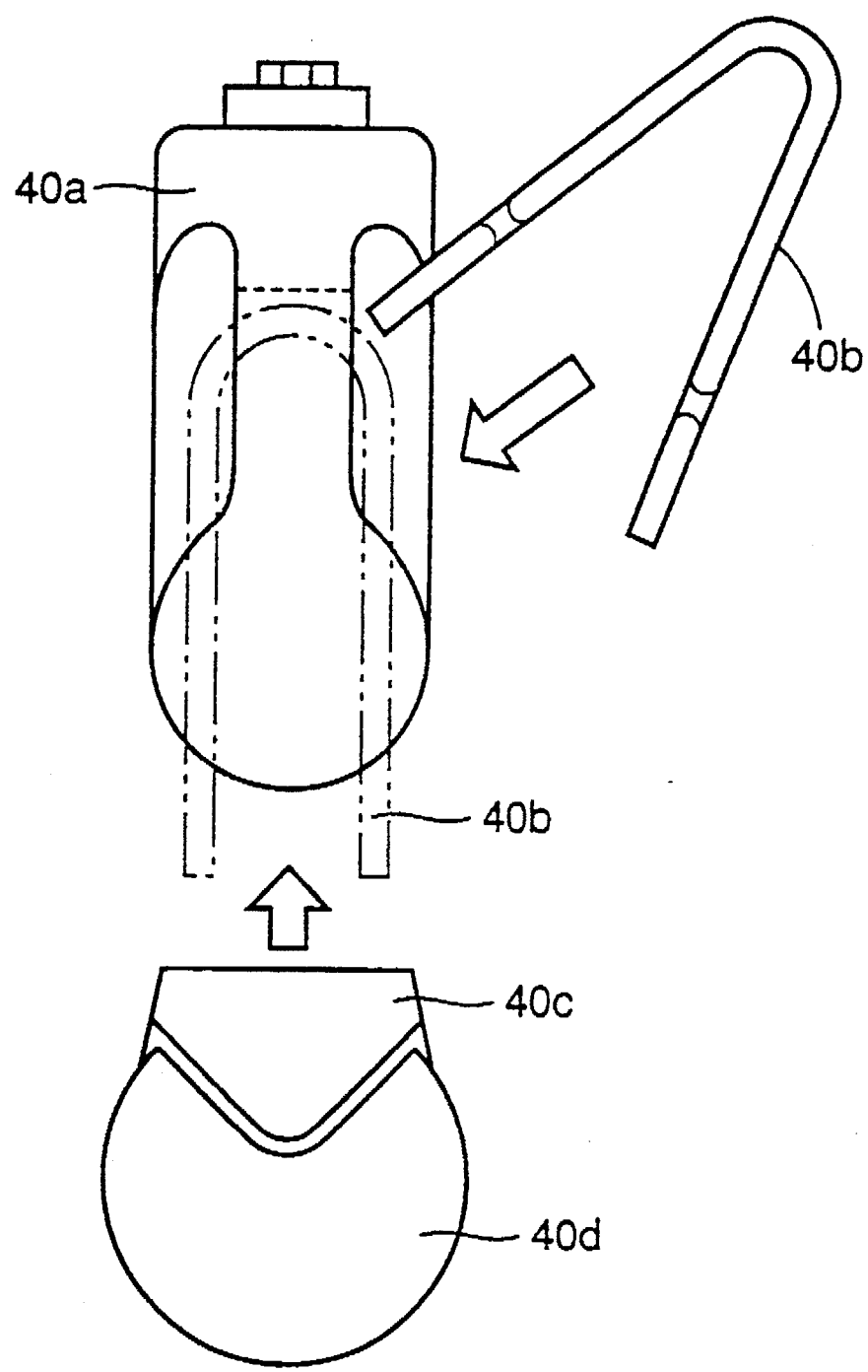
FIG. 28 is adapted to illustrate a state of assembling the ligative sutural member shown in FIG. 25.
Figure 29:
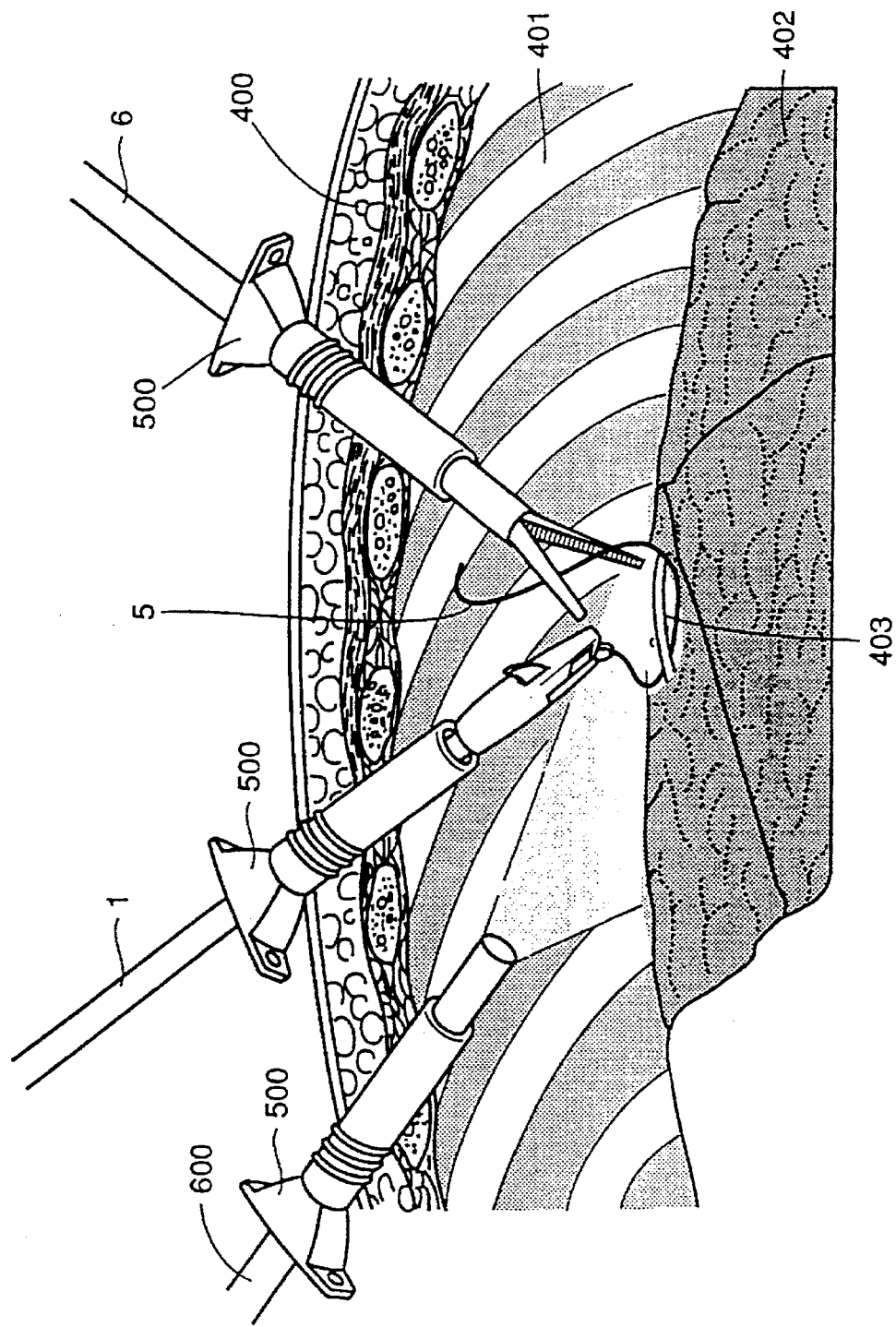
FIG. 29 is a model diagram for illustrating an endoscopic surgical operation.
Figure 30:
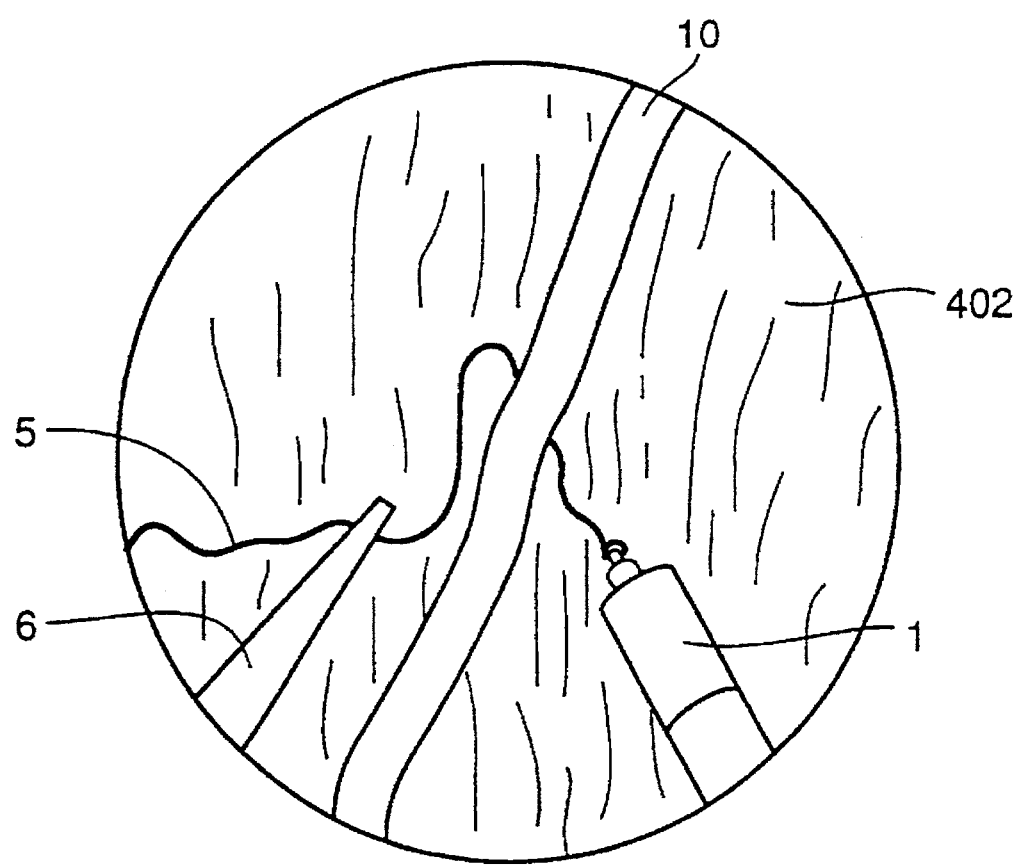
FIG. 30 is a model diagram showing the state of an affected portion which is projected on a monitor in the endoscopic surgical operation.
Figure 31:
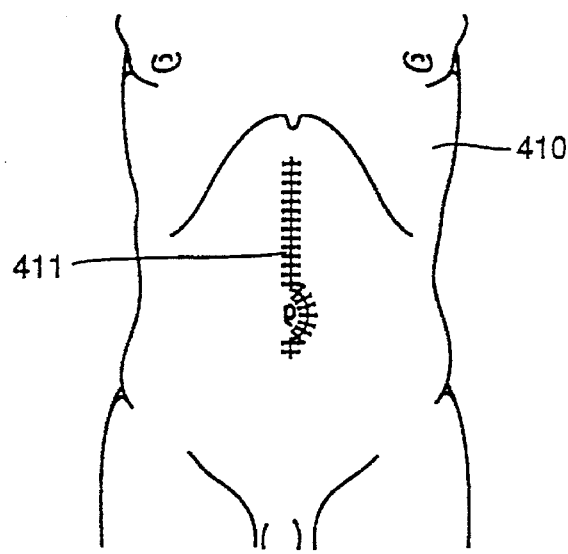
FIG. 31 illustrates the state of a wound which is formed on the body of a patient in an abdominal operation.
Figure 32:
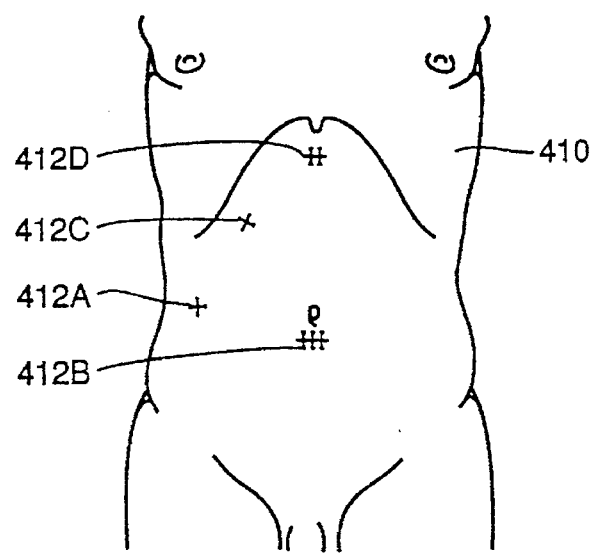
FIG. 32 illustrates the state of wounds which are formed on the body of a patient in a celioscopic operation.

In manufacturing of the ligative sutural member 40A having the aforementioned structure, the body part 40a can be formed as an integral substance by precutting, while the same can be formed by slightly spreading the clip 40b and inserting the same in the opening 40e toward the forward end and thereafter connecting the forward end of the clip 40b with the thread guard base 40c which is provided with the thread support part 40d, as shown in FIG. 28.

Also when the ligative sutural member 40A is employed, a functional effect which is similar to that of the aforementioned ligative sutural member 30A can be attained.

When the thread support part 304 or 40d of the aforementioned ligative sutural member 30A or 40A is in a color which is different from those of the remaining members, preferably in a color which is in contrast to that of blood, the operator can clearly recognize the thread support part 304 or 40d while observing a monitor. Consequently, the burden on the operator can be reduced.

The embodiments disclosed above are to be regarded as being not restrictive but illustrative in all points. While the ligative suturer according to the embodiment 2 has the most preferable structure having the mechanism of allowing protrusion of the thread guard member and that of bending the first and second rods, therefore, only the thread guard member may protrude or only the first and second rods may be bent, for example. Further, the mechanism for locking the first and second grips is not restricted to the aforementioned structure but may alternatively be in another well-known structure, to cause no problem.

Therefore, the present invention is shown not by the above description but by the scope of claims, and is intended to include equivalent meaning as the scope of claims and all modifications within the scope.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A ligative suturer comprising a ligative sutural member being provided on the forward end of a rod with a body part being of a substantially concave sectional shape along the axial direction of said rod and having an opening communicating with the forward end and right and left sides, and a movable body being provided in said opening of said body part with a trunk part being movably held by said body part, a forward end part protruding toward the forward end of said opening, and a thread support part being provided in the vicinity of its forward end for supporting an operative thread, for supporting a first side of said operative thread by said thread support part of said movable body and winding or sewing a second side of said operative thread around or on a portion to be operated along a prescribed rotational direction for arranging an intermediate portion of said operative thread on the upper side of said rod along said rotational direction while inserting said second side of said operative thread in said opening along said rotational direction, downwardly moving the same from above said movable body and drawing out said operative thread from said opening, thereby forming a knot of said operative thread on said portion to be operated, wherein said rod comprises:

a first rod being connected with said ligative sutural member, and a second rod being horizontally bendably connected with said first rod, said first rod is provided with:

a first rod member being connected with said ligative sutural member on its forward end, and a first connection block being provided to protrude from the rear end of said first rod member with a diameter being smaller than that of said first rod member, and having a first connection part being connected with said second rod on its rear end, and said second rod is provided with:

a second rod member being provided to be movable along the axial direction of said rod and capable of storing said first connection block protruding from said first rod member on its forward end, and having a first grip member on its rear end, a third rod member being stored in said second rod member for guiding movement of said second rod member in the axial direction of said rod on its outer peripheral surface and having a flange part on its rear end in a region being exposed from said second rod member, a first elastic member being provided on the outer peripheral surface of said third rod member between said first grip member and said flange part of said third rod member for regularly urging said second rod member toward the forward end, storing said first connection block and bringing the same into contact with the rear end of said first rod member, a fourth rod member having a forward end being stored in the rear end of said second rod member, a lever member having an end being pivotally supported on said forward end side to be horizontally movable, and a second grip member being provided on its rear end, a second elastic member being provided on the outer peripheral surface of said fourth rod member between said flange part of said third rod member and said second grip member for urging said fourth rod member toward the rear end with elastic force being larger than that of said first elastic member, first and second slide members having first and second slide blocks being stored in said third rod member on portions closer to the forward end than said lever member for horizontally holding said first connection part and being forwardly pushed by said lever member following movement of said fourth grip member toward the forward end, and first and second contact bars being provided on the forward ends of said first and second slide blocks respectively to be in contact with said first connection block, a second connection block being stored in the forward end of said third rod member and having a second connection part being horizontally movably connected with said first connection part and first and second guide passages storing said first and second contact bars therein for guiding sliding of said first and second contact bars on its forward end, and a third elastic member being provided on the outer peripheral surfaces of said first and second contact bars between said first and second slide blocks and said second connection block for regularly urging said first and second slide members toward the rear ends.

2. The ligative suturer in accordance with claim 1, being provided on the upper surface of said first rod with a thread guard for hanging said operative thread thereon for arranging said intermediate portion of said operative thread on the upper side of said rod.

3. The ligative suturer in accordance with claim 2, wherein said thread guard is provided with:

a thread guard member being provided in said first rod and rotated about a central axis being provided on said first connection block, for enabling protrusion and storage, a forwardly movable working bar being stored along guide grooves being horizontally provided to hold said first connection block to be pushed by said first or second contact bar toward the forward end following said forward movement of said first or second contact bar, an engaging pin being provided on said working pin to engage with said thread guard member so that said thread guard member protrudes following forward movement of said working bar, and storing said thread guard member following rearward movement of said working bar, and a fourth elastic member being provided between the forward end of said first rod member and said working bar for regularly urging said working bar toward the rear end.

4. The ligative suturer in accordance with claim 1, wherein said first and second grip members are provided with a locking mechanism for maintaining said first and second grip members in stationary states against urging force of said first and second elastic members when said first and second grip members are most approached to each other.

5. The ligative suturer in accordance with claim 4, wherein said locking mechanism comprises:

a guide surface being provided on said second grip member and including a locking groove including a first groove extending in the axial direction of said rod along the side surface of said first grip member and a second groove communicating with said first groove and extending in a direction perpendicular to said first groove, and a locking bar being provided on the side surface of said first grip member for engaging in said locking groove.

6. The ligative suturer in accordance with claim 1, wherein said first rod has an outwardly inclined surface so that a surface of said first rod to be in contact with said second rod comes into contact with said second rod in a most bent state of said first rod.

7. The ligative suturer in accordance with claim 1, wherein a member having a large coefficient of friction is mounted on a surface of said second rod to be in contact with said first rod.

8. The ligative suturer in accordance with claim 1, wherein only said thread support part is different in color from the remaining elements.

9. The ligative suturer in accordance with claim 1, wherein said ligative sutural member is detachably provided on the forward end of said first rod.

10. The ligative suturer in accordance with claim 9, wherein said ligative sutural member is provided with:

a neck portion, being provided on the rear end of said body part, having a smaller diameter than said body part, and first and second convex parts, having different widths, being provided around said neck portion on positions being outwardly opposite to each other, and said first rod is provided on its forward end with:

an opening being defined by a flange part having first and second window parts in positions corresponding to said first and second convex parts respectively for receiving said neck portion being provided on said body part, a contact plate being provided in said first rod for blocking said opening being provided in the forward end of said first rod, and a fifth elastic member for urging said contact plate toward the forward end of said first rod.

11. The ligative suturer in accordance with claim 10, wherein said fourth elastic member is identical to said fifth elastic member.

12. The ligative suturer in accordance with claim 1, wherein said body part is provided with:

an upper convex part being formed on the upper surface to downwardly extend from the forward end toward the rear end, a lower convex part being provided on the lower surface to be continuous with said upper convex part at a prescribed space, and a space part being defined in the rear end by said upper and lower convex parts, and said movable body has:

a substantially circular thread support part, being provided on its forward end, having a notched portion extending toward the forward end on its rear side, and a support hole, being provided on its rear end, for receiving said upper and lower convex parts with a prescribed space.

13. The ligative suturer in accordance with claim 12, wherein said movable body is so provided that said thread support part is downward beyond said support hole toward the forward end.

* * * * *